United States Patent [19]

Janssen et al.

[11] 4,005,218

[45] Jan. 25, 1977

[54] ANTIPARASITIC SALICYLANILIDE DERIVATIVES

[75] Inventors: Marcel A. C. Janssen, Vosselaar; Victor K. Sipido, Merksem, both of Belgium

[73] Assignee: Janssen Pharmaceutica N.V., Beerse, Belgium

[22] Filed: Jan. 13, 1976

[21] Appl. No.: 648,681

Related U.S. Application Data

[63] Continuation-in-part of Ser. No. 559,616, March 18, 1975, abandoned.

[52] U.S. Cl. .................... 424/304; 260/268 CN; 260/268 FT; 260/293.75; 260/329 AM; 260/329 ME; 260/438.1; 260/439 R; 260/465 D; 260/465 E; 260/465 F; 260/465 G; 260/465 R; 424/250; 424/267; 424/275

[51] Int. Cl.$^2$ ............... A61K 31/38; A61K 31/275; C07D 333/24; C07C 121/80

[58] Field of Search ............... 260/465 D, 329 AM; 424/304, 275

[56] References Cited

UNITED STATES PATENTS

3,798,258   3/1974   Patchett et al. ............... 260/465 X

*Primary Examiner*—Lewis Gotts
*Assistant Examiner*—Dolph H. Torrence
*Attorney, Agent, or Firm*—Salvatore R. Conte

[57] ABSTRACT

Compounds of the class of salicylanilides substituted in the 4-position of the anilino moiety with a —CH(CN)-Ar group wherein Ar is phenyl, substituted phenyl, thienyl, halothienyl or naphthalenyl, said salicylanilides being useful as parasiticides.

11 Claims, No Drawings

ANTIPARASITIC SALICYLANILIDE DERIVATIVES

CROSS-REFERENCE TO RELATED APPLICATIONS

This is a continuation-in-part of our copending application Ser. No. 559,616, filed Mar. 18, 1975, now abandoned.

BACKGROUND OF THE INVENTION

The invention pertains to the field of salicylanilide derivatives which demonstrate parasiticidal activity.

The subject salicylanilides differ from those of the prior art by, among other differences, the presence of an α-cyano-arylmethyl group, in the 4-position of the anilino moiety.

The prior art may be represented by the following references: British Pat. No. 1.183.461; and Belgium Pat. No. 796.406.

DESCRIPTION OF THE PREFERRED EMBODIMENTS

The novel salicylanilide derivatives of this invention may be structurally represented by the formula:

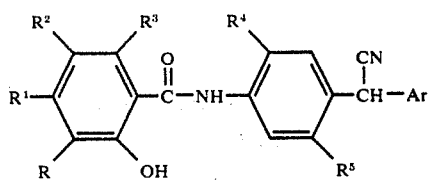
(I)

wherein:
R is a member selected from the group consisting of hydrogen, halo, lower alkyl and nitro;
$R^1$ is a member selected from the group consisting of hydrogen and halo;
$R^2$ is a member selected from the group consisting of hydrogen, halo, lower alkyl and nitro;
$R^3$ is a member selected from the group consisting of hydrogen, hydroxy and lower alkyl, provided that when said $R^3$ is hydroxy or lower alkyl then said $R^1$ is hydrogen;
$R^4$ is a member selected from the group consisting of hydrogen, halo and lower alkyl;
$R^5$ is a member selected from the group consisting of hydrogen, halo, lower alkyl, cyano and trifluoromethyl; and
Ar is a member selected from the group consisting of phenyl, substituted phenyl, thienyl, halothienyl and naphthalenyl, wherein said "substituted phenyl" represents phenyl having from 1 to 3 substituents independently selected from the group consisting of halo, lower alkyl, lower alkyloxy and trifluoromethyl.

As used herein, "lower alkyl" may be straight or branch chained and have from 1 to about 5 carbon atoms, such as, for example, methyl, propyl, isopropyl, butyl, tert-butyl, pentyl and the like and; the term "halo" is generic to bromo, fluoro, chloro and iodo. Among the preferred substituted phenyls represented by the symbol "Ar" are halophenyl, dihalophenyl, trihalophenyl, lower alkylphenyl, lower alkyloxyphenyl, trifluoromethylphenyl and halotrifluoromethylphenyl. The preferred "thienyl" is 2-thienyl and the preferred "halothienyl" is 5-chloro-2-thienyl.

Also within the scope of the present invention are the pharmaceutically acceptable replacement or amine addition salts of the compounds of formula (I).

Examples of such salts include metal salts such as, for example, sodium, potassium, calcium, copper and iron salts, and amine salts such as, for example, piperidine, piperazine, triethylamine, N-methylglucamine, methylamine, α-methylbenzylamine and ethanolamine salts.

The compounds of formula (I) may conveniently be prepared by the application of methodologies known in the art, more particularly, by procedures described in the literature for the preparation of salicylanilides.

Such procedures generally comprise the reaction of an appropriately substituted salicylic acid or a reactive functional derivative thereof with an appropriately substituted aniline or reactive derivative thereof under appropriate reaction conditions, for example as described in British Pat. No. 1.183.461.

A convenient method of preparing the compounds (I) consists in the condensation of an appropriately substituted salicylic acid halide of formula (II), preferably the chloride, wherein R, $R^1$, $R^2$ and $R^3$ are as previously indicated

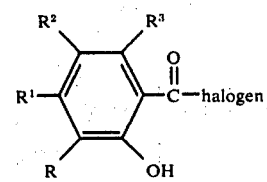
(II)

with an appropriately substituted amine of formula (III), wherein $R^4$, $R^5$ and Ar are as previously indicated, said amine being either in base form or in the form of an appropriate acid addition salt.

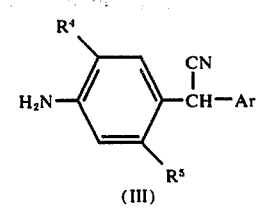
(III)

Said condensation reaction is carried out in a reaction-inert organic solvent from which the desired products of formula (I) are recovered by conventional procedures, for example, by evaporation of the solvent and recrystallization of the residue. Elevated temperatures and, preferably, reflux conditions may be employed to enhance the rate of the reaction. In order to pick up the acid which is liberated during the course of the reaction, there may be added an appropriate base such as, for example, N,N-diethylethanamine, pyridine and the like.

As used herein, the term "reaction-inert organic solvent" is meant to include any organic liquid which will not interfere with the interaction of the reactants (II) and (III) such as, for example, ethers, such as dioxane, tetrahydorfuran, diethylether and the like; aromatic hydrocarbons such as benzene, toluene, xylene and the like; and chlorinated hydrocarbons such as chloroform, methylene chloride and the like.

Alternatively the compounds (I) may be prepared by the reaction of (III) with an appropriate salicylic acid ester, preferably a phenyl ester of formula (IV) wherein R, R¹, R² and R³ have the same meaning as assigned to them previously.

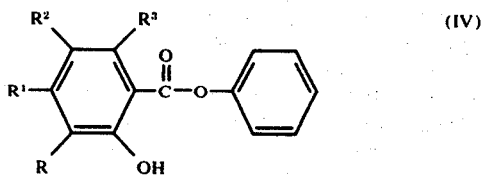

The reaction of (III) with (IV) is preferably carried out at elevated temperatures in an appropriate reaction-inert organic solvent such as, for example, 1,2,4-trichlorobenzene, 1,2-dichlorobenzene, nitrobenzene, diphenylether, diphenylmethane, tetrahydronaphthalene, decahydronaphthalene and the like.

Another convenient method of preparing the compounds (I) is by the reaction of an appropriate salicylic acid (V) wherein the substituents have the abovedefined meaning with a phosphoramide of formula (VI) wherein R⁴, R⁵ and Ar are as defined hereinbefore.

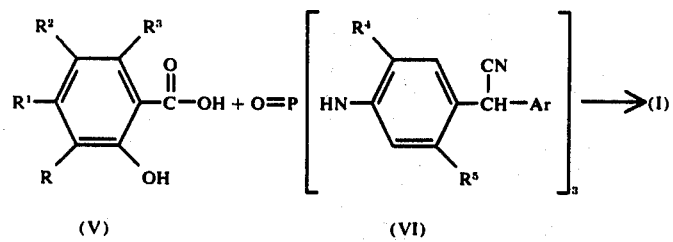

The phosphoramide (VI) which may be prepared in situ by the reaction of (III) with phosphoryl chloride, POCl₃, is reacted with the salicylic acid (V) by stirring the reactants together, preferably at elevated temperatures, in a suitable organic solvent such as, for example, an aliphatic hydrocarbon, e.g., hexane; cyclohexane and the like or a mixture of such hydrocarbons, e.g., petroleumether; an aromatic hydrocarbon, e.g., benzene, toluene, xylene and the like; a halogenated hydrocarbon, e.g., chloroform, methylene chloride, tetrachloroethane and the like or; a halogenated aromatic hydrocarbon, e.g., chlorobenzene, 1,2-dichlorobenzene, 1,2,4-trichlorobenzene and the like.

Still another method of preparing the compounds (I) is by the reaction of (V) with a compound of the formula (VII)

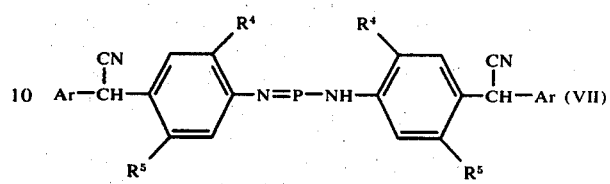

wherein R⁴, R⁵ and Ar are as previously defined in a similar manner as herebefore for the reaction of (V) with (VI).

The compounds of formula (VII) may conveniently be prepared, preferably in situ, by the reaction of (III) with phosphorous trichloride.

The compounds of formula (I) wherein R¹ and R³ are each hydrogen and R and R² are each iodo, (I-a), may still be prepared by iodinating a compound of formula (I) wherein R, R¹, R² and R³ are hydrogen, (I-b). Said iodination reaction is preferably carried out with iodine monochloride, previously prepared by the reaction of iodine with chlorine, in an acidic medium such as, for example in a mixture of acetic acid and water.

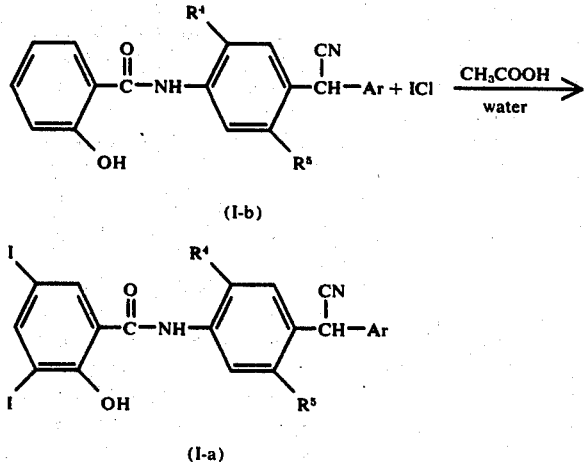

The salicylic acids of formula (V) as well as their halides (II) and esters, including the phenyl esters of formula (IV) are generally known and are obtained from procedures described in the literature.

The anilines of formula (III), a number of which are also known compounds, may be prepared from several synthetic routes. For example, they may conveniently be prepared by:

i. reacting an appropriate arylacetonitrile of formula (VIII) with an appropriately substituted 4-halonitrobenzene of formula (IX) in the presence of an appropriate strong base, in a suitable reaction-inert organic solvent as more specifically described hereafter, and ii. subsequently reducing the nitro function in the thus obtained (X) to an amine function using standard nitro-to-amine reduction procedures, for example, with zinc metal and acetic acid, with iron metal and ammonium chloride, with sodium dithionite or by catalytic hydrogenation, using, for example, palladium-on-charcoal catalyst.

Suitable bases to aid the reaction of (VIII) with (IX) include, for example, alkali metal amides and hydrides, such as, sodium amide and sodium hydride, respectively, and the like; alkali metal alkoxides such as, sodium ethanolate and the like; and alkali metal hydroxides such as, sodium hydroxide, potassium hydroxide and the like. Suitable solvents for this reaction include reaction-inert organic solvents such as, for example, aromatic hydrocarbons such as, benzene, toluene, xylene and the like, and ethers such as, dioxane, tetrahydrofuran, diethylether and the like. Good results have been obtained by using potassium hydroxide in pyridine.

A convenient and most preferred method of conducting the reaction of (VII) with (IX) is in a two-phase system as described, for example, by Makosza et al. in Tetrahedron, 30, 3723–3735 (1974). Typically in such type of reaction there is used concentrated aqueous alkali, e.g. 40–60% sodium hydroxide, and an appropriate water-immiscible reactioninert organic solvent such as, for example, benzene, toluene, xylene, tetrahydrofuran, methylene chloride and the like, in the presence of an appropriate quaternary ammonium catalyst, preferably N,N,N-triethylbenzenemethanaminium chloride, (BTEAC).

The foregoing reactions may be illustrated by the following schematic representation:

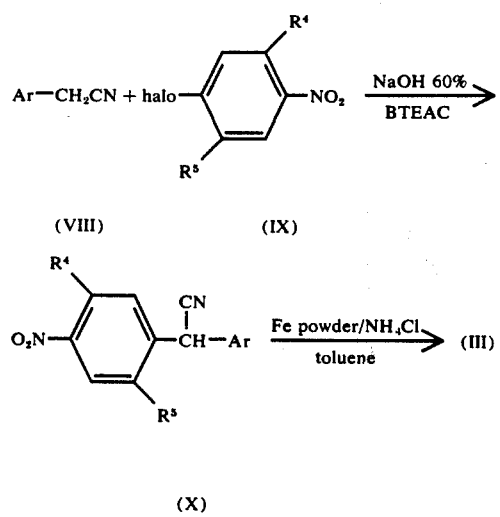

The amines of formula (III) may alternatively be prepared by the condensation of an arylacetonitrile of formula (VIII) with a nitrobenzene of formula (XI) to obtain a phenylcyanomethylene quinone oxime of formula (XII). The reduction of (XII) to obtain (III) may be carried out with an appropriate reducing agent such as, for example, zinc powder and acetic acid, iron powder and ammonium chloride, or by catalytic hydrogenation using, for example, palladium-on-charcoal catalyst.

The foregoing reactions are illustrated in the following schematic representation:

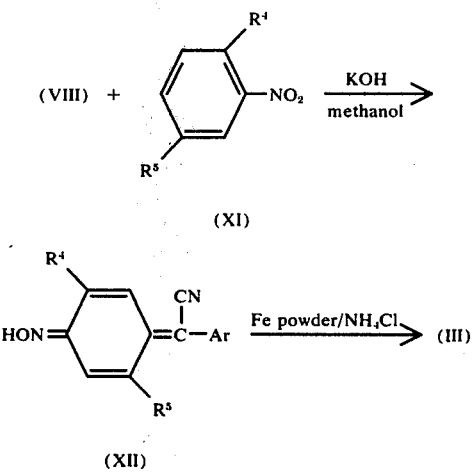

The starting materials of the formulas (VIII), (IX) and (XI) are generally known and may be prepared according to known procedures as described in the literature.

The compounds of formula (I) may, if desired, be converted into a pharmaceutically acceptable salt by the reaction with an appropriate base and from such salts the free salicylanilides may in turn be liberated by acid treatment.

The subject compounds of formula (I) have useful parasiticidal properties.

They are very potent anthelminthics, being very active against, for example, liver fluke, e.g. *Fasciola hepatica*, and against nematodes such as, for example, Haemonchus contortus in sheep and cattle.

Moreover they possess strong activity against a number of arthropod parasites such as, for example, *Oestrus ovis*, *Hypoderma bovis*, *Dermatobia hominis*, Lucillia etc.

In view of their broad spectrum of antiparasitic activity the compounds of this invention are valuable tools for the treatment of warm-blooded hosts, suffering from such parasites.

Accordingly, this invention embraces methods of killing parasites which comprise treating infected subjects with an effective antiparasitic amount of the novel compounds described herein. For this purpose about 1 to 200 milligrams per kilogram of body weight may be advantageously employed. Also within the scope of this invention are antiparasitical compositions comprising an effective anti-parasitical amount of the subject compounds in combination with suitable carriers.

The subject compounds can be used, for example, in the form of pharmaceutical and veterinarian preparations containing an anti-parasitical amount of a suitable organic or inorganic, solid or liquid pharmaceutical carrier, such as, for example, water, gelatine, lactose, starch, magnesium stearate, talc, vegetable oils, gums, polyalkylene glycols, etc..

The compositions are formulated by conventional methods and may be in any one of the conventional pharmaceutical forms, for example, for systemic application by way of oral or parenteral administration or for external application by direct contact onto the skin. Typical formulations include solutions, suspensions, emulsions, injectables, powders, slugs, granules, capsules, tablets, pellets and the like, including unit dosage forms thereof, as well as other convenient forms which might be suitable for veterinarian or human use. They may be sterilized, for example, for parenteral administration, and/or may contain assistants such as conventional excipients, preserving, stabilizing, wetting, dispersing, desintegrating or emulsifying agents, fillers, buffers, bacteriostats, bactericidal agents, sporicidal agents, thickening agents, preservatives, coloring agents, etc..

They may also contain further veterinary or therapeutically useful substances, including, for example, other known anthelminthics such as tetramisole, levamisole, mebendazole, thiabendazole, pyrvinium pamoate, piperazine citrate, 2-β-methoxy-ethylpyridine and the like. The subject compounds may also be used as additives and pre-mixes to animal feeds, drinking water, etc..

In such compositions and formulations, the concentration of the subject compound should be at least about 0.01%, and preferably at least about 0.05%, by weight. The concentration of compound may vary widely above these figures, depending on the form of composition taken, and indeed, in some cases the concentration of the compound may go as high as about 95%.

For example, compositions suitable for oral administration may be liquid or solid compositions. Suitable liquid compositions include, for example, aqueous concentrated solutions of the active ingredients, which solutions may optionally contain one or more buffers and/or stabilizing agents, for example sodium bisulfite, hydroxylamine or an acid addition salt thereof, for example the hydrochloride. The liquid compositions also include, for example solutions in a vegetable oil, for example arachis oil, dimethylacetamide, poly-alkylene glycols. The solid compositions include tablets, slugs, pellets or capsules, which may be formulated using conventional excipients. Alternatively, the solid compositions may be in the form of dispersible compositions containing at least one adsorbent solid, for example, fuller's earth or kieselguhr. The solid compositions may be in the form of pre-mix compositions suitable for addition to animal foodstuffs, or in the form of medicated animal foodstuff compositions, for example compositions comprising the active ingredients and animal foodstuffs. Compositions suitable for parenteral administration include, for example, sterile injectable aqueous and non-aqueous solutions or suspensions.

The invention may be illustrated by, although not limited to, the following examples. As used therein, unless otherwise stated, all parts are by weight.

EXAMPLE I

To a solution of 39 parts of potassium hydroxide in 39 parts of pyridine is added a solution of 17 parts of 1-chloro-4-nitrobenzene in 46 parts of pyridine. The whole is cooled to −5° C and there is added dropwise a solution of 22 parts of 2,4-dichlorobenzeneacetonitrile in pyridine, while still cooling at −5° C. Upon completion, stirring is continued for 10 hours at 0° C. After the addition of 90 parts of benzene, the product is precipitated. It is filtered off, washed on the filter with benzene and taken up in water. The aqueous mixture is treated with acetic acid, whereupon the product is separated as an oil. The latter is extracted with methylbenzene. The extract is dried, filtered and evaporated. The residue is crystallized from a mixture of methanol, 2,2'-oxybispropane, petroleumether and trichloromethane, yielding 2,4-dichloro-α-(4-nitrophenyl)benzeneacetonitrile; mp. 81°–82.5° C.

EXAMPLE II

To a stirred and warmed (30° C) mixture of 105 parts of 1-chloro-4-nitro-2-(trifluoromethyl)benzene, 10 parts of N,N,N-triethylbenzenemethanaminium chloride, 900 parts of sodium hydroxide solution 50% and 135 parts of tetrahydrofuran is added dropwise a mixture of 67.5 parts of 4-fluorobenzeneacetonitrile and 450 parts of tetrahydrofuran (exothermic reaction: temperature rises to 50° C). Upon completion, stirring is continued for 5 hours at 60° C. After cooling, the reaction mixture is poured onto crushed ice and the whole is acidified with a concentrated hydrochloric acid solution, while cooling. The product is extracted with methylbenzene. The extract is washed with water, dried filtered and evaporated. The residue is suspended in a mixture of 2,2'-oxybispropane and petroleumether. The product is filtered off, yielding α-(4-fluorophenyl)-4-nitro-2-(trifluoromethyl)-benzeneacetonitrile; mp. 68° C.

EXAMPLE III

Following the procedure of Example II and using equivalent amounts of the appropriate starting materials, the following nitrile compounds are prepared:
3,4-dichloro-α-(2-chloro-4-nitrophenyl)benzeneacetonitrile; mp. 105.8° C;
α-(4-bromophenyl)-4-nitro-2-(trifluoromethyl)benzeneacetonitrile; mp. 63.9° C;
α-(4-chlorophenyl)-2-cyano-4-nitrobenzeneacetonitrile as an oily residue;
4-chloro-α-[4-nitro-2-(trifluoromethyl)phenyl]-3-(trifluoromethyl)-benzeneacetonitrile; mp. 126.2° C;
4-nitro-2-(trifluoromethyl)-α-[3-(trifluoromethyl)phenyl]benzeneacetonitrile; mp. 88.4° C; and
2-chloro-α-[4-chloro-3-(trifluoromethyl)phenyl]-4-nitrobenzeneacetonitrile; mp. 110.2° C.

EXAMPLE IV

To a stirred mixture of 21 parts of 1-chloro-4-nitro-2-(trifluoromethyl)benzene, 180 parts of sodium hydroxide solution 60%, 2 parts of N,N,N-triethylbenzenemethanaminium chloride and 90 parts of tetrahydrofuran is added dropwise a mixture of 11.7 parts of benzeneacetonitrile and 27 parts of tetrahydrofuran at 30° C. Upon completion, stirring is continued for 4 hours at 50° C. After cooling, the reaction mixture is poured onto crushed ice. The whole is acidified with a hydrochloric acid solution (pH 1) while the temperature is kept below 20° C. The product is extracted with benzene. The extract is washed with water, dried, filtered and evaporated. The oily residue is crystallized from 70 parts of 2,2'-oxybispropane at 0° C, yielding 4-nitro-α-phenyl-2-(trifluoromethyl) benzeneacetonitrile; mp. 70.4° C.

EXAMPLE V

Following the procedure of Example IV and using equivalent amounts of the appropriate starting materials, the following nitrile compounds are prepared:

α-(4-chlorophenyl)-4-nitro-2-(trifluoromethyl)benzeneacetonitrile; mp. 60.2° C;

2,6-dichloro-α-[4-nitro-2-(trifluoromethyl)phenyl]-benzeneacetonitrile; m.p. 122.1° C;

2,4-dichloro-α-[4-nitro-2-(trifluoromethyl)phenyl]-benzeneacetonitrile; mp. 107° C;

α-(4-methoxyphenyl)-4-nitro-2-(trifluoromethyl)-benzeneacetonnitrile;

α-(4-methylphenyl)-4-nitro-2-(trifluoromethyl)benzeneacetonitrile; mp. 87.4° C;

3,4-dichloro-α-[4-nitro-2-(trifluoromethyl)phenyl]-benzeneacetonitrile; mp. 124° C;

2,6-dichloro-α-(2-chloro-4-nitrophenyl)benzeneacetonitrile; mp. 139.6° C;

2-chloro-α-(3-chlorophenyl)-4-nitrobenzeneacetonitrile; mp. 70° C; and 2-chloro-4-nitro-α-[3-(trifluoromethyl)phenyl]benzeneacetonitrile; mp. 123° C.

EXAMPLE VI 20 parts of iron-powder are added to 190 parts of ammonium chloride solution 0.78N at reflux temperature. Then there is added dropwise a solution of 20 parts of 2,4-dichloro-α-(4-nitrophenyl)benzeneacetonitrile in 180 parts of methylbenzene. Upon completion, stirring is continued overnight at reflux. The reaction mixture is cooled at 60° C and filtered over hyflo. The filter-cake is washed with tetrahydrofuran. The filtrate is dried, filtered and evaporated. The residue is converted into the hydrochloride salt in 2,2'-oxybispropane, methanol and 2-propanol. The salt is filtered off and dried, yielding α-(4-aminophenyl)-2,4-dichlorobenzeneacetonitrile hydrochloride; mp. 207.2° C.

EXAMPLE VII

Following the procedure of Example VI and using an equivalent amount of an appropriate α-aryl-4-nitrobenzeneacetonitrile in place of the 2,4-dichloro-α-(4-nitrophenyl)benzeneacetonitrile used therein, the following 4-amino-α-arylbenzeneacetonitriles or hydrochloride salts are prepared:

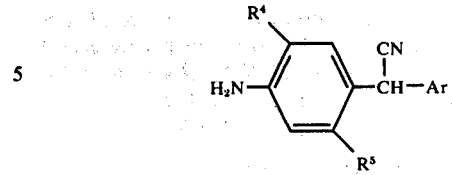

| R⁴ | R⁵ | Ar | Salt | mp. °C |
|---|---|---|---|---|
| H | Cl | 2,4-Cl₂—C₆H₃ | HCl | 220–227 |
| H | Cl | 3-Cl—C₆H₄ | — | 103.5 |
| H | Cl | 3-CF₃—4-Cl—C₆H₃ | — | 68.1 |
| H | Cl | 3-CF₃—C₆H₄ | — | 87.5 |
| H | CF₃ | 3-CF₃—4-Cl—C₆H₃ | — | 114 |
| H | CF₃ | 3-CF₃—C₆H₄ | — | 78.3 |
| H | CN | 4-Cl—C₆H₄ | — | 101.9 |
| H | CF₃ | 4-Br—C₆H₄ | — | 93.5 |
| H | Cl | 2,6-Cl₂—C₆H₃ | — | 123.7 |
| H | Cl | 3,4-Cl₂—C₆H₃ | — | 125.2 |
| H | CF₃ | 4-F—C₆H₄ | — |  |
| H | CF₃ | 4-Cl—C₆H₄ | — | 78 |
| H | CF₃ | 2,6-Cl₂—C₆H₃ | — | 162 |
| H | CF₃ | C₆H₅ | — | 124 |

-continued

| R⁴ | R⁵ | Ar | Salt | mp. °C |
|---|---|---|---|---|
| H | CF₃ | 4-OCH₃—C₆H₄ | — |  |
| H | CF₃ | 2,4-Cl₂—C₆H₃ | — |  |
| H | CF₃ | 3,4-Cl₂—C₆H₃ | — | 114.3 |
| H | CF₃ | 4-CH₃—C₆H₃ | — | 100.4 |
| Cl | Cl | 4-Cl—C₆H₄ | — | 130.4 |
| Cl | Cl | 2,4-Cl₂—C₆H₃ | — | 150.3 |

EXAMPLE VIII

To a stirred solution of 75 parts of potassium hydroxide in 240 parts of methanol, are added 27 parts of 2,4-dichlorobenzeneacetonitrile. Then there is added a solution of 25.5 parts of 1-chloro-4-methyl-3-nitrobenzene in 40 parts of methanol (exothermic reaction: temperature rises to 40° C). Stirring is continued for 2 hours while meantime the mixture is allowed to cool to 20°–25° C. 1000 parts of water are added. Upon the addition of a mixture of acetic acid and water (1:1 by volume), an oil is precipitated. The supernatant aqueous phase is decanted and the oil is taken up in methylbenzene. The solution is evaporated. The oily residue is triturated in a mixture of 2,2'-oxybispropane and petroleumether, yielding 2,4-dichloro-α-[2-chloro-4-(hydroxyimino)-5-methyl-2,5-cyclohexadien-1-ylidene]-benzeneacetonitrile.

370 parts of ammonium chloride solution 0.78N are stirred and heated to reflux. Then there are added 37 parts of iron-powder, followed by the dropwise addition of a solution of 37 parts of 2,4-dichloro-α-[2-chloro-4-(hydroxyimino)-5-methyl-2,5-cyclohexandien-1-ylidene]benzeneacetonitrile in 333 parts of methylbenzene. Upon completion, stirring at reflux is continued overnight. The reaction mixture is cooled to 60° C, filtered and the filter-cake is washed with tetrahydrofuran. The filtrate is dried, filtered and evaporated. The residue is converted into the hydrochloride salt in 2,2'-oxybispropane and 2-propanol, yielding 4-amino-2-chloro-α-(2,4-dichlorophenyl)-5-methylbenzeneacetonitrile hydrochloride.

EXAMPLE IX

A mixture of 40 parts of 4-chloro-α-[2-chloro-4-(hydroxyimino)-5-methyl-2,5-cyclohexadien-1-ylidene]-benzeneacetonitrile, 50 parts of iron-powder, 1500 parts of ammonium chloride solution 0.78N and 270 parts of methylbenzene is stirred and refluxed overnight. The reaction mixture is filtered over hyflo and the filter-cake is washed with 4-methyl-2-pentanone. The filtrate is dried, filtered and evaporated. The solid residue is crystallized from methylbenzene. The product is filtered off and recrystallized from methylbenzene, yielding 4-amino-2-chloro-α-(4-chlorophenyl)-5-methylbenzeneacetonitrile; mp. 152.6° C.

EXAMPLE X

A mixture of 4 parts of 2-hydroxy-3,5-diiodobenzoyl chloride, 2.9 parts of 4-amino-2-chloro-α-(4-chlorophenyl)-5-methylbenzeneacetonitrile and 75 parts of 1,4-dioxane is stirred and refluxed for 10 minutes. The reaction mixture is evaporated and the oily residue is crystallized from methanol. The product is filtered off and dried, yielding 5.3 parts of N-{5-chloro-4-[α-(4-chlorophenyl)-α-cyanomethyl]-2-methylphenyl}-2-hydroxy-3,5-diiodobenzamide; mp. 217.8° C.

EXAMPLE XI

Following the procedure of Example X and using equivalent amounts respectively of an appropriately substituted salicyloyl chloride and of an appropriately substituted 4-amino-α-aryl-benzeneacetonitrile or hydrochloride salt thereof, the following compounds of formula (I) were prepared:

| $R^1$ | $R^2$ | R | $R^4$ | $R^5$ | Ar | mp °C |
|---|---|---|---|---|---|---|
| H | I | I | H | H | 3-CH$_3$—C$_6$H$_4$ | 223–225 |
| H | I | I | H | H | 4-Cl—C$_6$H$_4$ | 238.2 |
| H | I | I | H | H | 4-CH$_3$—C$_6$H$_4$ | 244.9 |
| H | I | I | H | H | 4-OCH$_3$—C$_6$H$_4$ | 205.4 |
| H | I | I | H | Cl | 3,4-Cl$_2$—C$_6$H$_3$ | 240.6 |
| H | I | I | H | Cl | 2,6-Cl$_2$—C$_6$H$_3$ | 245.3 |
| H | I | I | H | Cl | 3-Cl—C$_6$H$_4$ | 205–206 |
| H | I | I | H | Cl | 2,4-Cl$_2$—C$_6$H$_3$ | 238.7 |
| H | I | I | H | H | 2,4-Cl$_2$—C$_6$H$_3$ | 238 |
| H | I | I | H | Cl | C$_6$H$_5$ | 199.1 |
| H | I | I | CH$_3$ | Cl | 2,4-Cl$_2$—C$_6$H$_3$ | 249 |
| Cl | Cl | Cl | H | H | 4-F—C$_6$H$_4$ | 247.8 |
| Cl | Cl | Cl | H | H | C$_6$H$_5$ | 259.1 |
| Cl | Cl | Cl | H | H | 4-OCH$_3$—C$_6$H$_4$ | 231.6 |
| Cl | Cl | Cl | H | H | 4-Cl—C$_6$H$_4$ | 244–245 |
| Cl | Cl | Cl | H | H | 3-CH$_3$—C$_6$H$_4$ | 249–250 |
| Cl | Cl | Cl | H | H | 4-CH$_3$—C$_6$H$_4$ | 254.2 |
| Cl | Cl | Cl | H | Cl | 4-Cl—C$_6$H$_4$ | 227.6 |
| Cl | Cl | Cl | H | Cl | 3,4-Cl$_2$—C$_6$H$_3$ | 216 |
| Cl | Cl | Cl | H | Cl | 2,6-Cl$_2$—C$_6$H$_3$ | 297 |
| Cl | Cl | Cl | H | Cl | 3-Cl—C$_6$H$_4$ | 248.2 |
| Cl | Cl | Cl | H | Cl | C$_6$H$_5$ | 244 |
| Cl | Cl | Cl | CH$_3$ | Cl | 4-Cl—C$_6$H$_4$ | 207.2 |
| Cl | Cl | Cl | CH$_3$ | Cl | 2,4-Cl$_2$—C$_6$H$_3$ | 244.1 |
| Cl | Cl | Cl | Cl | Cl | 4-Cl—C$_6$H$_4$ | 232 |
| H | I | I | Cl | Cl | 4-Cl—C$_6$H$_4$ | 242–247 |
| Cl | Cl | Cl | Cl | Cl | 2,4-Cl$_2$—C$_6$H$_3$ | 244.1 |
| H | I | I | Cl | Cl | 2,4-Cl$_2$—C$_6$H$_3$ | 219.6–221.2 |

EXAMPLE XII

A mixture of 8 parts of 3,5-diiodosalicyloyl chloride, 5.3 parts of 2-(4-aminophenyl)-2-(p-fluorophenyl)acetonitrile hydrochloride and 150 parts of dioxane is stirred and refluxed for 15 minutes. The reaction mixture is concentrated to a volume of about 50 parts. Upon the addition of 80 parts of methanol and 20 parts of water, the product is crystallized. It is filtered off and dried, yielding α-cyano-α-(p-fluorophenyl)-3,5-diiodosalicylo-p-toluidide; mp. 232° C (dec.).

EXAMPLE XIII

A mixture of 12 parts of 3,5-diiodosalicyloyl chloride, 8.3 parts of 2-(4-amino-2-chloro)-2-(p-chlorophenyl)acetonitrile and 150 parts of dioxane is stirred and refluxed for 15 minutes. The solvent is concentrated to about 50 parts of its volume. 160 parts of methanol and 5 parts of water are added and upon complete crystallization, the solid product is filtered off. It is washed with methanol and dried in vacuo at 100° C, yielding 3'-chloro-α-(p-chlorophenyl)-α-cyano-3,5-diiodo-p-salicylotoluidide; mp. 229° C.

EXAMPLE XIV

A solution of 4.9 parts of 2-hydroxy-3,5-diiodobenzoyl chloride and 3.7 parts of 4-amino-2-(trifluoromethyl)-α-[3-trifluoromethyl)phenyl]benzeneacetonitrile in 60 parts of 1,4-dioxane is stirred and refluxed for 10 minutes. The reaction mixture is evaporated. The residue is boiled in methylbenzene for 10 minutes. After cooling to room temperature, the precipitated product is filtered off, yielding N-[4-{α-cyano-α-[3-trifluoromethyl)phenyl]methyl-}3-(trifluoromethyl)-phenyl]-2-hydroxy-3,5-diiodobenzamide; mp. 206.3° C.

EXAMPLE XV

Following the procedure of Example XIV and using equivalent amounts of the appropriate starting materials the following compounds of formula (I) are prepared:

| $R^1$ | $R^2$ | R | $R^4$ | $R^5$ | Ar | mp. °C |
|---|---|---|---|---|---|---|
| H | I | I | H | CF$_3$ | C$_6$H$_5$ | 194.8 |
| H | I | I | H | CF$_3$ | 4-F—C$_6$H$_4$ | 207.1 |
| H | I | I | H | CF$_3$ | 4-Br—C$_6$H$_4$ | 213.3 |
| H | I | I | H | Cl | 3-CF$_3$—4-Cl—C$_6$H$_3$ | 210 |
| H | I | I | H | Cl | 3-CF$_3$—C$_6$H$_4$ | 184.4 |
| Cl | Cl | Cl | H | CF$_3$ | 3-CF$_3$—4-Cl—C$_6$H$_3$ | 219–221 |
| Cl | Cl | Cl | H | CF$_3$ | 3-CF$_3$—C$_6$H$_4$ | 208.2 |
| Cl | Cl | Cl | H | CF$_3$ | 4-Br—C$_6$H$_4$ | 199.5 |
| Cl | Cl | Cl | H | CF$_3$ | 4-F—C$_6$H$_4$ | 226–228 |
| Cl | Cl | Cl | H | CF$_3$ | C$_6$H$_5$ | 232.3 |
| Cl | Cl | Cl | H | Cl | 3-CF$_3$—4-Cl—C$_6$H$_3$ | 229 |

EXAMPLE XVI

A mixture of 9.8 parts of 2-hydroxy-3,5-diiodobenzoyl chloride, 7.6 parts of 4-amino-α-[4-chloro-3-(trifluoromethyl)phenyl]2-(trifluoromethyl)benzeneacetonitrile and 100 parts of 1,4-dioxane is stirred and refluxed for 10 minutes. The reaction mixture is evaporated. The residue solidifies on triturating in a mixture of methylbenzene, petroleumether and trichloromethane. The product is filtered off and crystallized from acetonitrile, yielding N-[4-{α-[4-chloro-3-(trifluoromethyl)phenyl]-α-cyanomethyl-}3-(trifluoromethyl)phenyl]-2-hydroxy-3,5-diiodobenzamide; mp. 203.3° C.

EXAMPLE XVII

A mixture of 3.5 parts of 3,5-dibromo-2-hydroxybenzoyl chloride, 3.47 parts of 4-amino-α-(2,4-dichlorophenyl)-2-(trifluoromethyl)benzeneacetonitrile and 50 parts of 1,4-dioxane is stirred and refluxed for 10 minutes. The reaction mixture is evaporated. The solid residue is boiled in a mixture of trichloromethane and 2,2'-oxybispropane. The product crystallizes after cooling, while stirring. It is sucked off, dried in vacuo at 110° C and recrystallized from acetonitrile, yielding 3,5-dibromo-N-{4-[α-cyano-α-(2,4-dichlorophenyl)methyl]-3-(trifluoromethyl)}-2-hydroxybenzamide; mp. 241.2° C.

EXAMPLE XVIII

Following the procedure of Example XVII and using equivalent amounts of the appropriate starting materials, the following compounds of formula (I) are prepared:

N-{4-[α-cyano-α-(3,4-dichlorophenyl)methyl]-3-(trifluoromethyl)phenyl}-2-hydroxy-3,5-diiodobenzamide; mp. 252.1° C (dec.);

N-{4-[α-cyano-α-(4methylphenyl)methyl]-3-(trifluoromethyl)phenyl}-2-hydroxy-3,5-diiodobenzamide; mp. 208.5° C;

3,4,5-trichloro-N-{4-[α-cyano-α-(2,4-dichlorophenyl)methyl]-3-(trifluoromethyl)phenyl}-2-hydroxybenzamide; mp. 109.9° C; and 3,4,5-trichloro-N-{4-[α-cyano-α-(4-methoxyphenyl)methyl]-3-(trifluoromethyl)phenyl}-2-hydroxybenzamide; mp. 219°–220° C.

EXAMPLE XIX

A mixture of 5 parts of 2-hydroxy-3,5-diiodobenzoyl chloride, 4 parts of 4-amino-α-(2,6-dichlorophenyl)-2-(trifluoromethyl)benzeneacetonitrile and 60 parts of 1,4-dioxane is stirred and refluxed for 10 minutes. The reaction mixture is evaporated and 1,1'-oxybisethane is added to the residue, whereupon the product is precipitated. It is crystallized from acetonitrile. The product is filtered off and dried in vacuo at 140° C, yielding N-{4-[α-cyano-α-(2,6-dichlorophenyl)methyl]-3-(trifluoromethyl)phenyl}-2-hydroxy-3,5-diiodobenzamide; mp. 247.8° C.

EXAMPLE XX

A mixture of 3.7 parts of 3,4,5-trichloro-2-hydroxybenzoyl chloride, 4.5 parts of 4-amino-α-(3,4-dichlorophenyl)-2-(trifluoromethyl)benzeneacetonitrile and 50 parts of 1,4-dioxane is stirred and refluxed for 10 minutes. The reaction mixture is evaporated and the residue is crystallized from 2,2'-oxybispropane. The product is filtered off, dried and recrystallized from acetonitrile. It is filtered off again and dried, yielding 3,4,5-trichloro-N-{4-[α-cyano-α-(3,4-dichlorophenyl)methyl]-3-(trifluoromethyl)phenyl}-2-hydroxybenzamide; mp. 146.5° C.

EXAMPLE XXI

A mixture of 3.1 parts of 3,4,5-trichloro-2-hydroxybenzoyl chloride, 3.5 parts of α-(4-aminophenyl)-2,4-dichlorobenzeneacetonitrile hydrochloride and 100 parts of 1,4-dioxane is stirred and refluxed for 25 minutes. The reaction mixture is evaporated. The residue solidifies on triturating in acetonitrile. The product is filtered off and dried, yielding 3,4,5-trichloro-N-{4-[α-cyano-α-(2,4-dichlorophenyl)methyl]phenyl}-2-hydroxybenzamide; mp. 142.8° C.

EXAMPLE XXII

A mixture of 4.9 parts of 2-hydroxy-3,5-diiodobenzoyl chloride, 2.7 parts of 4-amino-2-cyano-α-(4-chlorophenyl)benzeneacetonitrile and 60 parts of 1,4-dioxane is stirred and refluxed for 10 minutes. The reaction mixture is evaporated and the residue is crystallized from acetonitrile. The product is filtered off and dried, yielding N-{4-[α-(4-chlorophenyl)-α-cyanomethyl]-3-cyanophenyl}-2-hydroxy-3,5-diiodobenzamide; mp. 250°–252° C.

EXAMPLE XXIII

A mixture of 3.6 parts of 3,4,5-trichlorosalicyloyl chloride 3.9 parts of 4-amino-2-chloro-α-[3-(trifluoromethyl)phenyl]benzeneacetonitrile and 100 parts of 1,4-dioxane is stirred and refluxed for 10 minutes. The reaction mixture is evaporated and the residue is triturated in 2,2'-oxybispropane. The product is filtered off and dried, yielding 3,4,5-trichloro-N-[3-chloro-4-{α-cyano-α-[3-(trifluoromethyl)phenyl]methyl}phenyl]-2-hydroxybenzamide; mp. 233.1° C.

EXAMPLE XXIV

A mixture of 2.8 parts of 3,4,5-trichlorosalicyloyl chloride, 2.7 parts of 4-amino-2-cyano-α-(4-chlorophenyl)benzeneacetonitrile and 60 parts of 1,4-dioxane is stirred and refluxed for 10 minutes. The reaction mixture is evaporated and the residue solidifies on triturating in acetonitrile. The product is filtered off and dried, yielding 3,4,5-trichloro-N-{4-[α-(4-chlorophenyl)-α-cyanomethyl]-3-cyanophenyl}-2-hydroxybenzamide; mp. 247° C.

EXAMPLE XXV

A mixture of 8 parts of 2-hydroxy-3,5-diiodobenzoyl chloride, 5 parts of 4-amino-α-phenylbenzeneacetonitrile hydrochloride and 150 parts of 1,4-dioxane is stirred and refluxed for 15 minutes. The reaction mixture is filtered and the filtrate is evaporated. The oily residue is crystallized from ethanol, yielding N-[4-(α-cyano-α-phenylmethyl)phenyl]-2-hydroxy-3,5-diiodobenzamide; mp. 243.3° C.

EXAMPLE XXVI

A mixture of 7.28 parts of 3,4,5-trichloro-2-hydroxybenzoyl chloride, 10 parts of 4-amino-2-chloro-α-(2,4-dichlorophenyl)benzeneacetonitrile hydrochloride and 135 parts of 1,4-dioxane is stirred and refluxed for 2h.30. After cooling, the reaction mixture is evaporated. The residue solidifies on triturating in 68 parts of warm 2-propanol. The product is filtered off, yielding 3,4,5-trichloro-N-{3-chloro-4-[α-cyano-α-(2,4-dichlorophenyl)methyl]phenyl}-2-hydrobenzamide; mp. 240°–242° C.

EXAMPLE XXVII

A mixture of 3.6 parts of 3,4,5-trichlorosalicyloyl chloride, 3 parts of 4-amino-α-(4-chlorophenyl)-2-(trifluoromethyl)benzeneacetonitrile and 50 parts of 1,4-dioxane is stirred and refluxed for 10 minutes. The reaction mixture is evaporated. The residue is taken up in 2,2'-oxybispropane and the resulting oil is dissolved in methanol. The solution is evaporated and the residue is crystallized from a mixture of petroleumether, 2-propanol and trichloromethane. The product is filtered off and recrystallized from a mixture of methylbenzene and petroleumether, yielding 3,4,5-trichloro-N-{4-[α-(4-chlorphenyl)-α-cyanomethyl]-3-(trifluoromethyl)phenyl}-2-hydroxybenzamide; mp. 195°–197° C.

EXAMPLE XXVIII

A mixture of 5.3 parts of 3,4,5-trichlorosalicyloyl chloride, 5.8 parts of 4-amino-α-(4-methylphenyl)-2-(trifluoromethyl)benzeneacetonitrile and 50 parts of 1,4-dioxane is stirred and refluxed for 10 minutes. The reaction mixture is evaporated and the residue is crystallized from 2,2'-oxybispropane. The product is filtered off and dried at 170° C for 5 hours, yielding 3,4,5-trichloro-N-{4-[α-cyano-α-(4-methylphenyl)methyl]-3-(trifluoromethyl)phenyl}-2-hydroxybenzamide; mp. 202°–203° C.

EXAMPLE XXIX

A mixture of 5 parts of 2-hydroxy-3,5-diiodobenzoyl chloride, 4 parts of 4-amino-α-(2,4-dichlorophenyl)-2-(trifluoromethyl)benzeneacetonitrile and 60 parts of 1,4-dioxane is stirred and refluxed for 10 minutes. The reaction mixture is evaporated. The residue is crystallized from a mixture of 2-propanol and methylbenzene. The product is filtered off and dried, yielding N-{4-[α-cyano-α-(2,4-dichlorophenyl)methyl]-3-(trifluoromethyl)phenyl}-2-hydroxy-3,5-diiodobenzamide; mp. 220°–222° C.

EXAMPLE XXX

A mixture of 4.9 parts of 2-hydroxy-3,5-diiodobenzoyl chloride, 3 parts of 4-amino-α-(4-chlorophenyl)-2-(trifluoromethyl)benzeneacetonitrile and 60 parts of 1,4-dioxane is stirred and refluxed for 15 minutes. The reaction mixture is evaporated. The residue solidifies on triturating in 2,2'-oxybispropane. The product is dissolved in methylbenzene and the solution is boiled for 5 minutes. Upon cooling, the product is crystallized. It is filtered off and dried in vacuo at 140° C, yielding N-{4-[α-(4-chlorphenyl)-α-cyanomethyl]-3-(trifluoromethyl)phenyl}-2-hydroxy-3,5-diiodobenzamide; mp. 202.5°–203.5° C.

EXAMPLE XXXI

Following the procedure of Example X and using equivalent amounts of the appropriate starting materials, the following compounds of formula (I) may still be prepared:
  3,5-dibromo-N-{5-chloro-4-[α-(4-chlorophenyl)-α-cyanomethyl]2-methylphenyl}-2-hydroxybenzamide;
  3,5-dibromo-N-{5-chloro-4-[α-(4-chlorphenyl)-α-cyanomethyl]phenyl}-2-hydroxybenzamide;
  N-{2-chloro-4-[α-(4-chlorophenyl)-α-cyanomethyl]phenyl}-2-hydroxy-3,5-diiodobenzamide;
  3,4,5-trichloro-N-{2-chloro-4-[α-(4-chlorophenyl)-α-cyanomethyl]phenyl}-2-hydroxybenzamide;
  4-chloro-N-{5-chloro-4-[α-(4-chlorophenyl)-α-cyanomethyl]-2-methylphenyl}-2-hydroxy-3,5-diiodobenzamide;
  4-chloro-N-{5-chloro-4-[α-(4-chlorphenyl)-α-cyanomethyl]phenyl}-2-hydroxy-3,5-diiodobenzamide;
  3-bromo-4,5-dichloro-N-{5-chloro-4-[-α-(4-chlorphenyl)-α-cyanomethyl]2-methylphenyl}-2-hydroxybenzamide; and
  3-bromo-4,5-dichloro-N-{5-chloro-4-[α-(4-chlorophenyl)-α-cyanomethyl]phenyl}-2hydroxybenzamide.

EXAMPLE XXXII

A warm solution of 1 part of N-{5-chloro-4-[α-(4-chlorophenyl)-α-cyanomethyl]-2-methylphenyl}-2-hydroxy-3,5-diiodobenzamide, 0.3 parts of sodium hydroxide solution 10N, 8 parts of methanol and 10 parts of water is allowed to crystallize. The product is filtered off, washed with water and dried, yielding 0.7 parts (67.5%)of N-{5-chloro-4-[α-(4-chlorophenyl)-α-cyanomethyl]-2-methylphenyl}-2-hydroxy-3,5-diiodobenzamide, sodium salt hydrate; mp. 270°–300° C.

EXAMPLE XXXIII 0.65 Parts of N-{5-chloro-4-[α-(4-chlorophenyl)-α-cyanomethyl]-2-methylphenyl}-2-hydroxy-3,5-diiodobenzamide and 0.1 parts of piperidine are dissolved in 4 parts of methanol and 5 parts of 1,4-dioxane. The solvent is removed by evaporation in vacuo. The residue solidifies on triturating in 2,2'-oxybispropane. The product is filtered off and washed with 2,2'-oxybispropane, yielding, after drying, N-{5-chloro-4-[α-(4-chlorophenyl)-α-cyanomethyl]-2-methylphenyl}-2-hydroxy-3,5-diiodobenzamide compound with piperidine; mp. 140.3° C. (dec.).

EXAMPLE XXXIV 0.494 Parts of N-{5-chloro-4-[α-(4-chlorophenyl)-α-cyanomethyl]-2-methylphenyl}-2-hydroxy-3,5-diiodobenzamide and 0.1 parts of α-methylbenzenemethanamine are dissolved in 4 parts of methanol and 5 parts of 1,4-dioxane. The solvent is removed by evaporation in vacuo. The residue solidifies on triturating in 2,2'-oxybispropane. The product is filtered off, washed with 2,2'-oxybispropane and dried, yielding N-{5-chloro-4-[α-(4-chlorophenyl)-α-cyanomethyl]-2-methylphenyl}-2-hydroxy-3,5-diiodobenzamide compound with α-methylbenzenemethanamine; mp. 116.7° C. (dec.).

EXAMPLE XXXV

To a stirred and cooled (−5° C) mixture of 325 parts of nitric acid and 975 parts of a concentrated sulfuric acid solution are added dropwise 220 parts of 1,2-dichloro-4-(1,1-dimethylethyl)benzene. Upon completion, stirring is continued for 30 minutes at 5° C. The reaction mixture is poured onto water: the product precipitates as an oil. The supernatant aqueous water is decanted and the residual oil is extracted with trichloromethane. The extract is washed with water, dried, filtered and evaporated. The residue is crystallized from 2-propanol. The product is filtered off and recrystallized from 2-propanol, yielding 34.5 parts of 1,2-dichloro-4-(1,1-dimethylethyl)-5-nitrobenzene; mp. 80° C.

EXAMPLE XXXVI

Following the procedure of Example XXXV and using an equivalent amount of 1,2-dichloro-4-(1-methylethyl)benzene in place of the 1,2-dichloro-4-(1,1-dimethylethyl)benzene used therein, there is obtained:
  1,2-dichloro-4-(1-methylethyl)-5-nitrobenzene; mp. <50° C.

EXAMPLE XXXVII

Following the procedure of Example IV and using equivalent amounts of the appropriate starting materials, the following nitrile compounds are prepared:
  3,4-dimethoxy-α-[4-nitro-2-(trifluoromethyl)phenyl]benzeneacetonitrile; mp. 96°–103° C;
  α-(2-chloro-4-nitrophenyl)-2-naphtaleneacetonitrile; mp. 171.7° C;
  α-[4-nitro-2-(trifluoromethyl)phenyl]-2-naphthaleneacetonitrile; mp. 120° C;
  α-(2-chloro-4-nitrophenyl)-2-thiopheneacetonitrile as an oily residue;

5-chloro-α-(2-chloro-5-methyl-4-nitrophenyl)-2-thiopheneacetonitrile as an oily residue;

5-chloro-α-(2-chloro-4-nitrophenyl)-2-thiopheneacetonitrile as an oily residue;

2-chloro-α-(4-chlorophenyl)-5-(1,1-dimethylethyl)-4-nitrobenzeneacetonitrile as a residue; and 2-chloro-α-(4-chlorophenyl)-5-(1-methylethyl)-4-nitrobenzeneacetonitrile; mp. 111° C.

EXAMPLE XXXVIII

Following the procedure of Example VI and using an equivalent amount of an appropriate α-aryl-4-nitrobenzeneacetonitrile in place of the 2,4-dichloro-α-(4-nitrophenyl)benzeneacetonitrile used therein, the following 4-amino-α-aryl-benzeneacetonitriles or hydrochloride salts are prepared:

4-amino-α-(3,4-dimethoxyphenyl)-2-(trifluoromethyl)benzeneacetonitrile; mp. 168° C;

α-[4-amino-2-(trifluoromethyl)phenyl]-2-naphthaleneacetonitrile hydrochloride;

α-(4-amino-2-chlorophenyl)-2-naphthaleneacetonitrile;

α-(4-amino-2-chlorophenyl)-2-thiopheneacetonitrile; mp. 87° C;

α-(4-amino-2-chloro-5-methylphenyl)-5-chloro-2-thiopheneacetonitrile; mp. 147° C;

α-(4-amino-2-chlorophenyl)-5-chloro-2-thiopheneacetonitrile hydrochloride; mp. 130° C;

4-amino-2-chloro-α-(4-chlorophenyl)-5-(1,1-dimethylethyl)benzeneacetonitrile as a residue; and 4-amino-2-chloro-α-(4-chlorophenyl)-5-(1-methylethyl)benzeneacetonitrile hydrochloride.

EXAMPLE XXXIX

A mixture of 4.5 parts of 2-hydroxy-3,5-diiodobenzoyl chloride, 3 parts of 4-amino-α-(4-methoxyphenyl)-2-(trifluoromethyl)benzeneacetonitrile and 50 parts of 1,4-dioxane is stirred and refluxed for 5 minutes. The reaction mixture is evaporated and the residue is crystallized from a mixture of 75 parts of trichloromethane and 35 parts of 2,2'-oxybispropane, yielding 6.5 parts of N-{4-[α-cyano-α-(4-methoxyphenyl)methyl]-3-(trifluoromethyl)phenyl}-2-hydroxy-3,5-diiodobenzamide; mp. 198°–200° C.

EXAMPLE XL

Following the procedure of Example X and using equivalent amounts of the appropriate starting materials, the following compounds are prepared:

N-{3-chloro-4-[α-cyano-α-(2-thienyl)methyl]phenyl}-2-hydroxy-3,5-diiodobenzamide; mp. 233.6° C;

3,4,5-trichloro-N-{3-chloro-4-[α-cyano-α-(2-thienyl)methyl]phenyl}-2-hydroxybenzamide; mp. 229.9° C;

3,4,5-trichloro-N-{5-chloro-4-[α-(5-chloro-2-thienyl)-α-cyanomethyl]-2-methylphenyl}-2-hydroxybenzamide; mp. 209°–211° C; and N-{5-chloro-4-[α-(5-chloro-2-thienyl)-α-cyanomethyl]-2-methylphenyl}-2-hydroxy-3,5-diiodobenzamide; mp. 180.3° C.

EXAMPLE XLI

Following the procedure of Example XIV and using equivalent amounts of the appropriate starting materials, the following compounds are prepared:

N-{3-chloro-4-[α-(4-chlorophenyl)-α-cyanomethyl]phenyl}-2-hydroxybenzamide; mp. 173.5° C; and 3,4,5-trichloro-N-{4-[α-cyano-α-(2-naphthalenyl)methyl]-3-(trifluoromethyl)phenyl}-2-hydroxybenzamide hemihydrate; mp. 221.7° C.

EXAMPLE XLII

Following the procedure of Example X and using equivalent amounts of the appropriate starting materials, the following compounds are obtained after crystallization in a mixture of methanol and 1,1'-oxybisethane:

3,4,5-trichloro-N-{3-chloro-4-[α-(5-chloro-2-thienyl)-α-cyanomethyl]phenyl}-2-hydroxybenzamide; mp. 205.4° C; and N-{3-chloro-4-[α-(5-chloro-2-thienyl)-α-cyanomethyl]phenyl}-2-hydroxy-3,5-diiodobenzamide; mp. 180°–183° C.

EXAMPLE XLIII

A mixture of 4.4 parts of 2-hydroxy-3,5-diiodobenzoyl chloride, 2.9 parts of α-(4-amino-2-chlorophenyl)-2-naphthaleneacetonitrile and 50 parts of 1,4-dioxane is stirred and refluxed for 10 minutes. The reaction mixture is evaporated. The residue is triturated in methanol. The product is filtered off, boiled in ethyl acetate and filtered off again, yielding 4.5 parts (68%) of N-{3-chloro-4-[α-cyano-α-(2-naphthalenyl)methyl]phenyl}-2-hydroxy-3,5-diiodobenzamide; mp. 263.8° C.

EXAMPLE XLIV

A mixture of 2.8 parts of 3,4,5-trichlorosalicyloyl chloride, 2.9 parts of α-(4-amino-2-chlorophenyl)-2-naphtaleneacetonitrile and 50 parts of 1,4-dioxane is stirred and refluxed for 10 minutes. The reaction mixture is evaporated. The residue solidifies in boiling methanol. The product is filtered off and boiled in ethyl acetate. It is filtered off again and dried, yielding 3.5 parts (67%) of 3,4,5-trichloro-N-{3-chloro-4-[α-cyano-α-(2-naphthalenyl)methyl]phenyl}-2-hydroxybenzamide; mp. 249.2° C.

EXAMPLE XLV

A mixture of 4.4 parts of 2-hydroxy-3,5-diiodobenzoyl chloride, 3.6 parts of α-[4-amino-2-(trifluoromethyl)phenyl]-2-naphthaleneacetonitrile hydrochloride and 50 parts of 1,4-dioxane is stirred and refluxed for 10 minutes. The reaction mixture is evaporated. The residue solidifies in boiling methylbenzene. After cooling, the product is filtered off and boiled in acetonitrile. It is filtered off again and dried at 120° C/10⁻³, yielding 4.5 parts (64%) of N-{4-[α-cyano-α-(2-naphthalenyl)methyl]-3-(trifluoromethyl)phenyl}-2-hydroxy-3,5-diiodobenzamide; mp. 249.3° C.

EXAMPLE XLVI

A mixture of 2.3 parts of 2-hydroxybenzoyl chloride, 4.1 parts of 4-amino-α-(4-methylphenyl)-2-(trifluoromethyl)-benzeneacetonitrile and 50 parts of 1,4-dioxane is stirred and refluxed for 10 minutes. The reaction mixture is evaporated and the residue is boiled in methylbenzene. The product is filtered off and dissolved in a mixture of acetonitrile and methanol. The solution is filtered and the filtrate is evaporated. The solid residue is stirred with acetonitrile. The product is filtered off and dried, yielding 2.6 parts of N-{4-[α- cyano-α-(4-methylphenyl)methyl]-3-(trifluoromethyl)phenyl}-2-hydroxybenzamide; mp. 165.5° C.

EXAMPLE XLVII

A mixture of 3.1 parts of 2-hydroxybenzoyl chloride, 4.2 parts of 4-amino-α-phenylbenzeneacetonitrile and 100 parts of 1,4-dioxane is stirred and refluxed for 2 hours. Then there are added 0.7 parts of N,N-diethylethanamine and the whole is evaporated. The oily residue is triturated in methylbenzene. The product is filtered off and crystallized from methylbenzene, yielding 2.3 parts of N-{4-(α-cyano-α-phenylmethyl)phenyl]-2-hydroxybenzamide; mp. 176.8° C.

EXAMPLE XLVIII

A mixture of 3.1 parts of 2-hydroxybenzoyl chloride, 6.7 parts of 4-amino-α-(3,4-dimethoxyphenyl)-2-(trifluoromethyl)-benzeneacetonitrile and 100 parts of 1,4-dioxane is stirred and refluxed till HCl-gas evolution is ceased (duration: ±2 hours). The reaction mixture is evaporated. The oily residue is taken up in acetonitrile. After cooling, the precipitated product is filtered off and dissolved in a boiling mixture of 2-propanone and methanol. The whole is filtered while hot and the filtrate is evaporated. The residue is crystallized from methanol. The product is filtered off and dried in vacuo at 140° C, yielding 1.1 parts of N-{4-[α-cyano-α-(3,4-dimethoxyphenyl)methyl]-3-(trifluoromethyl)-phenyl}-2-hydroxybenzamide; mp. 194.6° C.

EXAMPLE IL

A mixture of 3.1 parts of 2-hydroxybenzoyl chloride, 4.4 parts of 4-amino-α-(4-methylphenyl)benzeneacetonitrile and 100 parts of 1,4-dioxane is stirred and refluxed for one hour: during this reflux-time 0.7 parts of N,N-diethylethanamine are added. The reaction mixture is evaporated. The residue is stirred in ethanol. The product is filtered off and crystallized from ethyl acetate. It is filtered off again and dissolved in 2-propanone. The solution is filtered and the filtrate is evaporated, yielding 0.9 parts of N-{4-[α-cyano-α-(4-methylphenyl)methyl]phenyl}-2-hydroxybenzamide; mp. 157.4° C.

EXAMPLE L

A mixture of 6.5 parts of 3,5-diiodo-2-hydroxybenzoyl chloride, 5.3 parts of 4-amino-2-chloro-α-(4-chlorophenyl)-5-(1,1-dimethylethyl)benzeneacetonitrile and 60 parts of 1,4-dioxane is stirred and refluxed for 30 minutes. The reaction mixture is evaporated. The residue is purified by column-chromatography over silica gel using trichloromethane as eluent. The pure fractions are collected and the eluent is evaporated. The residue is crystallized from methylbenzene. The product is filtered off and dried, yielding 2.2 parts of N-{5-chloro-4-[α-(4-chlorophenyl)-α-cyanomethyl]-2-(1,1-dimethylethyl)phenyl}-2-hydroxy-3,5-diiodobenzamide; mp. 149.1° C.

EXAMPLE LI

A mixture of 2.9 parts of 3,4,5-trichloro-2-hydroxybenzoyl chloride, 3.3 parts of 4-amino-2-chloro-α-(4-chlorophenyl)-5-(1,1-dimethylethyl)benzeneacetonitrile and 60 parts of 1,4-dioxane is stirred and refluxed for 20 minutes. The reaction mixture is evaporated and the residue is purified by column-chromatography over silica gel using trichloromethane as eluent. The pure fractions are collected and the eluent is evaporated. The residue is crystallized from 2,2'-oxybispropane. The product is filtered off and dried in vacuo at 100° C/10⁻³ mm., yielding 3.5 parts of 3,4,5-trichloro-N-{5-chloro-4-[α-(4-chlorophenyl)-α-cyanomethyl]-2-(1,1-dimethylethyl)phenyl}-2-hydroxybenzamide; mp. 231.9° C.

EXAMPLE LII

A mixture of 4.4 parts of 3,4,5-trichloro-2-hydroxybenzoyl chloride, 5.4 parts of 4-amino-2-chloro-α-(4-chlorophenyl)-5-(1-methylethyl)benzeneacetonitrile hydrochloride and 70 parts of 1,4-dioxane is stirred and refluxed for 40 minutes. The reaction mixture is evaporated and the residue is crystallized from 2,2'-oxibispropane. The product is filtered off and dried, yielding 6.3 parts of 3,4,5-trichloro-N-{5-chloro-4-[α-(4-chlorophenyl)-α-cyanomethyl]-2-(1-methylethyl)phenyl}-2-hydroxybenzamide; mp. 207.1° C.

EXAMPLE LIII

A mixture of 4.8 parts of 2-hydroxy-3,5-diiodobenzoyl chloride, 6.5 parts of 4-amino-2-chloro-α-(4-chlorophenyl)-5-(1-methylethyl)benzeneacetonitrile hydrochloride and 60 parts of 1,4-dioxane is stirred and refluxed for 30 minutes. The reaction mixture is evaporated and the residue is purified by column-chromatography over silica gel using a mixture of trichloromethane, hexane and methanol (50:50:5) as eluent. The pure fractions are collected and the eluent is evaporated. The residue is crystallized from acetonitrile, yielding 4.2 parts of N-{5-chloro-4-[α-(4-chlorophenyl)-α-cyanomethyl]-2-(1-methylethyl)phenyl}-2-hydroxy-3,5-diiodobenzamide; mp. 200.6° C.

EXAMPLE LIV

A mixture of 9.2 parts of phenyl 2,6-dihydroxybenzoate, 9 parts of 4-amino-α-(4-fluorophenyl)benzeneacetonitrile and 30 parts of 1,2,4-trichlorobenzene is stirred for 10 minutes at 200° C. The reaction mixture is cooled and upon the addition of 150 parts of trichloromethane, the product is crystallized. It is filtered off, washed with trichloromethane and dried, yielding 11.4 parts of N-{4-[α-cyano-α-(4-fluorophenyl)-methyl]phenyl}-2,6-dihydroxybenzamide; mp. 239° C.

EXAMPLE LV

Following the procedure of Example LIV and using equivalent amounts of the appropriate starting materials, the following compounds are prepared:
  N-{4-[α-cyano-α-(4-methylphenyl)methyl]phenyl}-2,6-dihydroxybenzamide; mp. 211.4° C;
  N-[3-chloro-4-(α-cyano-α-phenylmethyl)phenyl]-2,6-dihydroxybenzamide; mp. 229.5° C;
  N-[4-(α-cyano-α-phenylmethyl)phenyl]-2,6-dihydroxybenzamide; mp. 229.3° C; and N-{4-[α-cyano-α-(4-methoxyphenyl)methyl]phenyl}-2,6-dihydroxybenzamide; mp. 199.6° C.

EXAMPLE LVI

A mixture of 4.14 parts of phenyl 2,6-dihydroxy-3-nitrobenzoate, 5.25 parts of 4-amino-α-(2,4-dichlorophenyl)-2-(trifluoromethyl)benzeneacetonitrile and 30 parts of 1,2,4-trichlorobenzene is stirred for 10 minutes at 195° C. The reaction mixture is poured onto 105 parts of 2,2'-oxybispropane while stirring. The precipitated product is filtered off, washed with 2,2'-oxybispropane and crystallized from a mixture of acetonitrile and 2,2′-oxybispropane. The product is filtered off and dried in vacuo at 110° C, yielding 6.07 parts of N-{4-[α-cyano-α-(2,4-dichlorophenyl)methyl]-3-(trifluoromethyl)phenyl}-2,6-dihydroxy-3-nitrobenzamide; mp. 220.9° C.

EXAMPLE LVII

Following the procedure of Example LVI and using equivalent amounts of the appropriate starting materials, the following compounds are prepared:

N-{4-[α-cyano-α-(4-methoxyphenyl)methyl]-3-(trifluoromethyl)-phenyl}-2,6-dihydroxy-3-nitrobenzamide; mp. 200° C; and N-[3-chloro-4-{α-cyano-α-[3-(trifluoromethyl)-phenyl]methyl}-phenyl]-2,6-dihydroxybenzamide; mp. 240.5° C.

EXAMPLE LVIII

A mixture of 3.5 parts of phenyl 3-bromo-2,6-dihydroxy-5-nitrobenzoate, 3.5 parts of 4-amino-α-(2,4-dichlorophenyl)-2-(trifluoromethyl)benzeneacetonitrile and 22.5 parts of 1,2,4-trichlorobenzene is stirred for 10 minutes at 190° C. The reaction mixture is allowed to cool to room temperature and poured onto 140 parts of petroleumether. The supernatant phase is decanted and the residual solid product is crystallized from acetonitrile. It is sucked off and dried in vacuo at 110° C, yielding 3.9 parts of 3-bromo-N-{4-[α-cyano-α-(2,4-dichlorophenyl)methyl]-3-(trifluoromethyl)-phenyl}-2,6-dihydroxy-5-nitrobenzamide; mp. 246.6° C.

EXAMPLE LIX

Following the procedure of Example LVIII there is prepared 3-bromo-N-{4-[α-cyano-α-(4-methoxyphenyl)methyl]-3-(trifluoromethyl)phenyl}-2,6-dihydroxy-5-nitrobenzamide; mp. 197° C by the reaction of phenyl 3-bromo-2,6-dihydroxy-5-nitrobenzoate with 4-amino-α-(4-methoxyphenyl)-2-(trifluoromethyl)-benzeneacetonitrile.

EXAMPLE LX

A mixture of 2.3 parts of phenyl 2,6-dihydroxybenzoate, 3 parts of 4-amino-α-(4-methoxyphenyl)-2-(trifluoromethyl)benzeneacetonitrile and 22.5 parts of 1,2,4-trichlorobenzene is stirred for 10 minutes at 190° C. The reaction mixture is poured onto petroleumether. The supernatant phase is decanted and the residual crude product is boiled in methylbenzene. The solution is stirred in activated charcoal. The latter is filtered off and 2,2′-oxybispropane is added to the filtrate till turbid. The product is allowed to crystallize while stirring, filtered off and recrystallized from acetonitrile, yielding 1.5 parts of N-{4-[α-cyano-α-(4-methoxyphenyl)methyl]-3-(trifluoromethyl)phenyl}-2,6-dihydroxybenzamide; mp. 181.5° C.

EXAMPLE LXI

Following the procedure of Example LX there is prepared N-{4-[α-cyano-α-(2,4-dichlorophenyl)methyl]-3-(trifluoromethyl)-phenyl}-2,6-dihydroxybenzamide; mp. 199.5° C, by the reaction of phenyl 2,6-dihydroxybenzoate with 4-amino-α-(2,4-dichlorophenyl)-2-(trifluoromethyl)benzeneacetonitrile.

EXAMPLE LXII

A mixture of 4.5 parts of phenyl 3-chloro-2,6-dihydroxy-5-nitrobenzoate, 4.5 parts of 4-amino-α-(4-chlorophenyl)-2-(trifluoromethyl)benzeneacetonitrile and 37.5 parts of 1,2,4-trichlorobenzene is stirred for 10 minutes at 180° C. After cooling, the reaction mixture is poured onto petroleumether, whereupon the product is separated as an oil. The supernatant phase is decanted and discarded. The oily product solidifies after stirring for 30 minutes in a mixture of 150 parts of trichloromethane and 70 parts of petroleumether. The solid product is filtered off and crystallized from 75 parts of trichloromethane (activated charcoal), yielding 2.7 parts of 3-chloro-N-{4-[α-(4-chlorophenyl)-α-cyanomethyl]-3-(trifluoromethyl)phenyl}-2,6-dihydroxy-5-nitrobenzamide; mp. 186.1° C.

EXAMPLE LXIII

Following the procedure of Example LXII there is prepared N-{4-[α-cyano-α-(4-fluorophenyl)methyl]-3-(trifluoromethyl)phenyl}-2,6-dihydroxybenzamide; mp. 206.4° C, by the reaction of phenyl 2,6-dihydroxybenzoate with 4-amino-α-(4-fluorophenyl)-2-(trifluoromethyl)benzeneacetonitrile.

EXAMPLE LXIV

A mixture of 3 parts of phenyl 3-chloro-2,6-dihydroxy-5-nitrobenzoate, 3.5 parts of 4-amino-α-(2,4-dichlorophenyl)-2-(trifluoromethyl)benzeneacetonitrile and 30 parts of 1,2,4-trichlorobenzene is stirred for 10 minutes at 190° C. The reaction mixture is poured onto 140 parts of petroleumether. The supernatant organic phase is decanted. The residue is boiled in methylbenzene and stirred with activated charcoal. The latter is filtered off over hyflo and petroleumether is added to the filtrate till turbid. The product is allowed to crystallize on standing. It is filtered off and dried in vacuo at 100° C, yielding 3 parts of 3-chloro-N-{4-[α-cyano-α-(2,4-dichlorophenyl)methyl]-3-(trifluoromethyl)phenyl}-2,6-dihydroxy-5-nitrobenzamide; mp. 224.7° C.

EXAMPLE LXV

A mixture of 3.5 parts of phenyl 2,6-dihydroxybenzoate, 4.5 parts of 4-amino-α-(4-chlorophenyl)-2-(trifluoromethyl)benzeneacetonitrile and 22.5 parts of 1,2,4-trichlorobenzene is stirred at 200° C for 20 minutes. The reaction mixture is cooled and poured onto 140 parts of petroleumether. The supernatant phase is decanted and the residual oil is dissolved in 75 parts of trichloromethane. 175 Parts of petroleumether are added and the whole is boiled for 30 minutes while stirring. The product is filtered off and crystallized from 235 parts of benzene, yielding 2.5 parts of N-{4-[α-(4-chlorophenyl)-α-cyanomethyl]-3-(trifluoromethyl)phenyl}-2,6-dihydroxybenzamide; mp. 187.7° C.

EXAMPLE LXVI

A mixture of 4.7 parts of phenyl 2,6-dihydroxybenzoate, 7.24 parts of 4-amino-α-(3,4-dichlorophenyl)-2-(trifluoromethyl)benzeneacetonitrile and 15 parts of 1,2,4-trichlorobenzene is stirred for 10 minutes at 180°–200° C. After cooling, the reaction mixture is poured onto petroleumether. The resulting oil is separated and boiled in a mixture of petroleumether and trichloromethane, while stirring. The solid product is filtered off and crystallized from methylbenzene, yielding 3 parts of N-{4-[α-cyano-α-(3,4-dichlorophenyl)-methyl]-3-(trifluoromethyl)phenyl}-2,6-dihydroxybenzamide; mp. 189.7° C.

EXAMPLE LXVII

A mixture of 5.16 parts of phenyl 2,6-dihydroxybenzoate, 6.6 parts of 4-amino-α-(4-methylphenyl)-2-trifluoromethyl)benzeneacetonitrile and 75 parts of 1,2,4-trichlorobenzene is stirred for 10 minutes at 180°–200° C. The reaction mixture is cooled and poured onto petroleumether. The supernatant oily product is separated and boiled in a mixture of petroleumether and trichloromethane. The resulting solution is cooled and the product is filtered off. It is purified by column-chromatography over silica gel, using a mixture of trichloromethane and 5% of methanol as eluent. The pure fractions are collected and the eluent is evaporated, yielding 1 part of N-{4-[α-cyano-α-(4-methylphenyl)methyl]-3-(trifluoromethyl)phenyl}-2,6-dihydroxybenzamide; mp. 212.5° C

EXAMPLE LXVIII

A mixture of 4.6 parts of phenyl 2,6-dihydroxybenzoate, 5.6 parts of 4-amino-α-phenyl-2-(trifluoromethyl)-benzeneacetonitrile and 26 parts of 1,2,4-trichlorobenzene is stirred for 15 minutes at 200° C. After cooling, the reaction mixture is poured onto 140 parts of petroleumether, whereupon an oil is precipitated. The supernatant phase is decanted and the residual oil is dissolved in trichloromethane. The solution is boiled in 140 parts of petroleumether for 30 minutes, while stirring. The precipitated product is filtered off and purified by column-chromatography over silica gel using a mixture of trichloromethane and 5% of methanol as eluent. The pure fractions are collected and the eluent is evaporated. The residue is crystallized from 180 parts of methylbenzene, yielding 3.8 parts of N-[4-(α-cyano-α-phenylmethyl)-3-(trifluoromethyl)-phenyl]-2,6-dihydroxybenzamide; mp. 201° C.

EXAMPLE LXIX

A mixture of 6 parts of phenyl 3-bromo-2,6-dihydroxy-5-nitrobenzoate, 4.5 parts of 4-amino-α-(4-chlorophenyl)-2-(trifluoromethyl)benzeneacetonitrile and 22.5 parts of 1,2,4-trichlorobenzene is stirred and boiled at 190°–200° C for 10 minutes. After cooling, the reaction mixture is poured onto 140 parts of petroleumether, whereupon an oil is precipitated. The supernatant phase is decanted and the residual oil is dissolved in 75 parts of trichloromethane and 45 parts of methylbenzene, 140 Parts of petroleumether are added and the whole is boiled for 30 minutes while stirring. The precipitated product is filtered off and crystallized from 30 parts of trichloromethane. The product is filtered off and washed with trichloromethane, yielding 3 parts of 3-bromo-N-{4-[α-(4-chlorophenyl)-α-cyanomethyl]-3-(trifluoromethyl)phenyl}-2,6-dihydroxy-5-nitrobenzamide; mp. 200.7° C.

EXAMPLE LXX

A mixture of 3 parts of phenyl 3-chloro-2,6-dihydroxy-5-nitrobenzoate, 3 parts of 4-amino-α-(4-methoxyphenyl)-2-(trifluoromethyl)benzeneacetonitrile and 30 parts of 1,2,4-trichlorobenzene is stirred for 10 minutes at 190° C. The reaction mixture is cooled and poured onto 140 parts of petroleumether while stirring. The supernatant phase is decanted and the residue is boiled in methylbenzene and stirred with activated charcoal. The latter is filtered off over hyflo. Petroleumether is added to the filtrate till turbid and the product is allowed to crystallize while stirring. It is filtered off, dried and crystallized from acetonitrile, yielding 4.5 parts of 3-chloro-N-{4-[α-cyano-α-(4-methoxyphenyl)methyl]-3-trifluoromethyl)phenyl}-2,6-dihydroxy-5-nitrobenzamide; mp. 206.4° C.

EXAMPLE LXXI

A mixture of 2.3 parts of phenyl 2,6-dihydroxybenzoate, 2.7 parts of 4-amino-2-cyano-α-(4-chlorophenyl)-benzeneacetonitrile and 22.5 parts of 1,2,4-trichlorobenzene is stirred and refluxed for 10 minutes. The reaction mixture is cooled and poured onto petroleumether: whereupon an oil is precipitated. The supernatant phase is decanted and the residual oil solidifies on triturating in a mixture of petroleumether and trichloromethane. The product is filtered off and boiled in 40 parts of acetonitrile, yielding 1.5 parts of N-{4-[α-(4-chlorophenyl)-α-cyanomethyl]-3-cyanopheny}-2,6-dihydroxybenzamide; mp. + 300° C (dec.).

EXAMPLE LXXII

A mixture of 4.5 parts of phenyl 2,6-dihydroxybenzoate, 4.2 parts of 4-amino-2-chloro-α-(4-chlorophenyl)-benzeneacetonitrile and 22.5 parts of 1,2,4-trichlorobenzene is stirred for 10 minutes at 180°–200° C. The reaction mixture is poured onto petroleumether, whereupon the product is precipitated as an oil. The supernatant phase is decanted and the residual oil is crystallized from 150 parts of trichloromethane, yielding 4.5 parts of N-{3-chloro-4-[α-(4-chlorophenyl)-α-cyanomethyl]phenyl}-2,6-dihydroxybenzamide; mp. 162.8° C.

EXAMPLE LXXIII

A mixture of 6.9 parts of phenyl 2,6-dihydroxybenzoate, 10.6 parts of 4-amino-α-(4-bromophenyl 2-(trifluoromethyl)benzeneacetonitrile and 30 parts of 1,2,4-trichlorobenzene is stirred for 20 minutes at 180° C. The reaction mixture is cooled and poured onto petroleumether. The supernatant phase is decanted and the residual oil is taken up in 2,2'-oxybispropane and petroleumether. The whole is filtered and the filtrate is evaporated. The oily residue is taken up in trichloromethane and petroleumether. The product is filtered off and crystallized from methylbenzene, yielding 5 parts of N-{4-[α-(4-bromophenyl)-α-cyanomethyl]-3-(trifluoromethyl)phenyl}-2,6-dihydroxybenzamide; mp. 190.6° C.

EXAMPLE LXXIV

To a stirred and hot (60° C) mixture of 4 parts of 3-(1,1-dimethylethyl)-2-hydroxy-6-methyl-5-nitrobenzoic acid, 7.5 parts of 4-amino-2-chloro-α-[3-(trifluoromethyl)phenyl]benzeneacetonitrile and 66 parts of chlorobenzene is added dropwise a solution of 1.5 parts of phosphoryl chloride in 11 parts of chlorobenzene. Upon completion, stirring is continued for 2 hours at reflux temperature. The reaction mixture is poured onto trichloromethane and the whole is filtered over hyflo. The filtrate is evaporated. The residue is purified by column-chromatography over silica gel using a mixture of hexane, trichloromethane and methanol (50:50:5) as eluent. The pure fractions are collected and the eluent is evaporated. The residue is crystallized from a mixture of trichloromethane and petroleumether, yielding 4 parts of N-[3-chloro-4-{α-cyano-α-[3-(trifluoromethyl)phenyl]methyl}phenyl]-3-(1,1-dimethylethyl)-2-hydroxy-6-methyl-5-nitrobenzamide; mp. 118.6° C.

EXAMPLE LXXV

Following the procedure of Example LXXIV there is prepared N-{4-[α-cyano-α-(2,4-dichlorophenyl)methyl]phenyl}-3-(1,1-dimethylethyl)-2-hydroxy-6-methyl-5-nitrobenzamide; mp. 175.9° C by the reaction of 3-(1,1-dimethylethyl)-2-hydroxy-6-methyl-5-nitrobenzoic acid with α-(4-aminophenyl)-2,4-dichlorobenzeneacetonitrile.

EXAMPLE LXXVI

To a stirred and hot mixture of 4 parts of 3-(1,1-dimethylethyl)-2-hydroxy-6-methyl-5-nitrobenzoic acid, 4 parts of 4-amino-2-chloro-α-(4-chlorophenyl)-benzeneacetonitrile and 55 parts of chlorobenzene is added dropwise a solution of 1 part of phosphoryl chloride in 11 parts of chlorobenzene at 60° C. Upon completion, stirring is continued for 6 hours at reflux. The reaction mixture is filtered while hot. The filtrate is allowed to cool and poured onto 750 parts of petroleumether: the product separates as an oil. The supernatant phase is decanted and the residual oil is dissolved in 1,1'-oxybisethane. The solution is saturated with gaseous hydrogen chloride and filtered over hyflo. The filtrate is washed with water, dried, filtered and evaporated. The residue is purified by column-chromatography over silica gel using trichloromethane as eluent. The pure fractions are collected and the eluent is evaporated. The residue is crystallized from a mixture of trichloromethane and petroleumether. The product is filtered off and dried at 100° C/10⁻³ mm., yielding 3.3 parts of N-{3-chloro-4-[α-(4-chlorophenyl)-α-cyanomethyl]phenyl}-3-(1,1-dimethylethyl)-2-hydroxy-6-methyl-5-nitrobenzamide; mp. 185.4° C.

EXAMPLE LXXVII

To a stirred mixture of 4 parts of 3-(1,1-dimethylethyl)-2-hydroxy-6-methyl-5-nitrobenzoic acid, 6.9 parts of 4-amino-2-chloro-α-(4-chlorophenyl)-5-methylbenzeneacetonitrile and 55 parts of chlorobenzene is added dropwise a solution of 1.5 parts of phosphoryl chloride in 11 parts of chlorobenzene at 60° C. Upon completion, stirring is continued for 3 hours. The reaction mixture is cooled and poured onto 450 parts of petroleumether. The latter is decanted and the residual precipitate is boiled in 350 parts of 1,1'-oxybisethane. The solution is saturated with gaseous hydrogen chloride and filtered over hyflo. The filtrate is washed twice with water, dried, filtered and evaporated. The residue is crystallized from methylbenzene, yielding 4 parts (47%) of N-{5-chloro-4-[α-(4-chlorophenyl)-α-cyanomethyl]-2-methylphenyl}-3-(1,1-dimethylethyl)-2-hydroxy-6-methyl-5-nitrobenzamide; mp. 133.4° C.

EXAMPLE LXXVIII

To a stirred and hot (60° C) mixture of 4 parts of 3-(1,1-dimethylethyl)-2-hydroxy-6-methyl-5-nitrobenzoic acid, 17.5 parts of 4-amino-2,5-dichloro-α-(4-chlorophenyl)benzeneacetonitrile and 55 parts of chlorobenzene is added dropwise a solution of 1.5 parts of phosphoryl chloride in 11 parts of chlorobenzene. Upon completion, stirring is continued for 3 hours at reflux temperature. The reaction mixture is cooled and poured onto 350 parts of petroleumether. The precipitate is filtered off and the product is allowed to crystallize from the filtrate. It is filtered off and dried, yielding 3 parts of N-{2,5-dichloro-4-[α-(4-chlorophenyl)-α-cyanomethyl]phenyl}-3-(1,1-dimethylethyl)-2-hydroxy-6-methyl-5-nitrobenzamide; mp. 161.2° C.

EXAMPLE LXXIX

To a stirred and hot (60° C) mixture of 3 parts of 3-(1,1-dimethylethyl)-2-hydroxy-6-methyl-5-nitrobenzoic acid, 6.2 parts of 4-amino-2-(trifluoromethyl)-α-[3-(trifluoromethyl)phenyl]benzeneacetonitrile and 55 parts of chlorobenzene is added dropwise a solution of 1.3 parts of phosphoryl chloride in 11 parts of chlorobenzene. Upon completion, stirring is continued for 3 hours at reflux temperature. The reaction mixture is cooled and poured onto 350 parts of petroleumether. The product is filtered off and dissolved in 1,1'-oxybisethane. The solution is saturated with gaseous hydrogen chloride and filtered over hyflo. The filtrate is evaporated. The residue is purified by column-chromatography over silica gel using a mixture of hexane, trichloromethane and methanol (10:10:1 by volume) as eluent. The pure fractions are collected and the eluent is evaporated. The residue is crystallized from a mixture of trichloromethane and petroleumether, yielding 1.2 parts of N-[4-{α-cyano-α-[3-(trifluoromethyl)phenyl]methyl}-3-(trifluoromethyl)phenyl]-3-(1,1-dimethylethyl)-2-hydroxy-6-methyl-5-nitrobenzamide; mp. 146.7° C.

EXAMPLE LXXX

To a stirred and hot (60° C) mixture of 4 parts of 3-(1,1-dimethylethyl)-2-hydoxy-6-methyl-5-nitrobenzoic acid, 7.5 parts of 4-amino-α-(4-chlorophenyl)-2-(trifluoromethyl)benzeneacetonitrile and 55 parts of chlorobenzene is added dropwise a solution of 1.5 parts of phosphoryl chloride in 11 parts of chlorobenzene. Upon completion, stirring is continued for 3 hours at reflux temperature. The reaction mixture is cooled and poured onto petroleumether: the product precipitates as an oil. The supernatant phase is decanted and the residual oil is taken up in 1,1'-oxybisethane. The solution is saturated with gaseous hydrogen chloride and filtered over hyflo. The filtrate is washed with water, dried, filtered and evaporated. The residue is crystallized from a mixture of trichloromethane and petroleumether. The product is filtered off and recrystallized from acetonitrile, yielding 3.8 parts of N-{4-[α-(4-chlorophenyl)-α-cyanomethyl]-3-(trifluoromethyl)phenyl}-3-(1,1-dimethylethyl)-2-hydroxy-6-methyl-5-nitrobenzamide; mp. 211.8° C.

EXAMPLE LXXXI

To a stirred and hot (60° C) mixture of 4 parts of 3-(1,1-dimethylethyl)-2-hydroxy-6-methyl-5-nitrobenzoic acid, 8.5 parts of 4-amino-α-(4-bromophenyl)-2-(trifluoromethyl)benzeneacetonitrile and 55 parts of chlorobenzene is added dropwise a solution of 1.5 parts of phosphoryl chloride in 22 parts of chlorobenzene. Upon completion, stirring is continued for 3 hours at reflux temperature. The reaction mixture is cooled and filtered over hyflo. The filtrate is poured onto 350 parts of petroleumether: the product precipitates as an oil. The supernatant phase is decanted and the residual oil is taken up in 350 parts of 1,1'-oxybisethane. The solution is saturated with gaseous hydrogen chloride and filtered over hyflo. The filtrate is washed with water, dried, filtered and distilled azeotropically with methylbenzene. The solvent is evaporated and the residue is crystallized from a mixture of trichloromethane and petroleumether. The product is filtered off and recrystallized from methylbenzene, yielding 3.4 parts of N-{4-[α-(4-bromophenyl)-α-cyanomethyl]-3-(trifluoromethyl)phenyl}-3-(1,1-dimethylethyl)-2-hydroxy-6-methyl-5-nitrobenzamide; mp. 211.5° C.

EXAMPLE LXXXII

To a stirred solution of 5 parts of 3-(1,1-dimethylethyl)-2-hydroxy-5-iodo-6-methylbenzoic acid and 5 parts of 4-amino-α-(4-chlorophenyl)-2-(trifluoromethyl)benzeneacetonitrile in 55 parts of chlorobenzene is added dropwise a solution of 1.25 parts of phosphoryl chloride in 11 parts of chlorobenzene while heating at 60° C. Upon completion, stirring is continued for 2 hours at 120° C. After cooling to 60° C, another portion of 2.5 parts of 4-amino-α-(4-chlorophenyl)-2-(trifluoromethyl)benzeneacetonitrile are added and the whole is stirred for 2 hours at 120° C. The reaction mixture is cooled and 300 parts of trichloromethane are added. The solution is filtered over hyflo and the filtrate is washed with a sodium carbonate solution 5%, dried, filtered and evaporated. The residue is purified by column-chromatography over silica gel using a mixture of trichloromethane, 50% of hexane and 5% of methanol as eluent. The pure fractions are collected and the eluent is evaporated. The residue is crystallized from cyclohexane, yielding 2.5 parts of N-{4-[α-(4-chlorophenyl)-α-cyanomethyl]-3-(trifluoromethyl)-phenyl}-3-(1,1-dimethylethyl)-2-hydroxy-5-iodo-6-methylbenzamide; mp. 154.3° C.

EXAMPLE LXXXIII

To a stirred and hot (60° C) mixture of 4 parts of 3-(1,1-dimethylethyl)-2-hydroxy-6-methyl-5-nitrobenzoic acid and 6.2 parts of 4-amino-2-chloro-α-(2,4-dichlorophenyl)-5-methylbenzeneacetonitrile in 55 parts of chlorobenzene is added dropwise a solution of 1.5 parts of phosphoryl chloride in 17 parts of chlorobenzene. Upon completion, stirring is continued for 3 hours at 140° C. The reaction mixture is cooled and poured onto 375 parts of trichloromethane. The whole is filtered over hyflo. The filtrate is washed with water, dried, filtered and evaporated. The residue is crystallized from a mixture of trichloromethane and petroleumether. The product is filtered off and recrystallized from methylbenzene, yielding, after drying at 100° C/10⁻³ mm., 6 parts of N-{5-chloro-4-[α-cyano-α-(2,4-dichlorophenyl)methyl]-2-methylphenyl}-3-(1,1-dimethylethyl)-2-hydroxy-6-methyl-5-nitrobenzamide; mp. 141.9° C.

EXAMPLE LXXXIV

To a stirred and hot (60° C) mixture of 4 parts of 3-(1,1-dimethylethyl)-2-hydroxy-6-methyl-5-nitrobenzoic acid, 6.6 parts of 4-amino-α-phenyl-2-(trifluoromethyl)benzeneacetonitrile and 55 parts of chlorobenzene is added dropwise a solution of 1.5 parts of phosphoryl chloride in 17 parts of chlorobenzene. Upon completion, stirring is continued for 2.50 hours at reflux temperature. The reaction mixture is cooled and poured onto 300 parts of trichloromethane. The whole is filtered and the filtrate is evaporated. The residue is crystallized from a mixture of 150 parts of trichloromethane and and 140 parts of petroleumether. The product is filtered off and dried, yielding 4 parts of N- 4-(α-cyano-α-phenylmethyl)-3-(trifluoromethyl)-phenyl]-3-(1,1-dimethylethyl)-2-hydroxy-6-methyl-5-nitrobenzamide; mp. 188.8° C.

EXAMPLE LXXXV

To a stirred and hot (60° C) mixture of 4 parts of 3-(1,1-dimethylethyl)-2-hydroxy-6-methyl-5-nitrobenzoic acid, 6.5 parts of 4-amino-2-cyano-α-(4-chlorophenyl)benzeneacetonitrile and 66 parts of chlorobenzene are added 1.5 parts of phosphoryl chloride and the whole is stirred and refluxed for 2 hours. The reaction mixture is cooled and poured onto trichloromethane. The whole is filtered and the filtrate is evaporated. The residue is crystallized from a mixture of trichloromethane and petroleumether, yielding 7 parts (88%) of N-{4-[α-(4-chlorophenyl)-α-cyanomethyl]-3-cyanophenyl}-3-(1,1-dimethylethyl)-2-hydroxy-6-methyl-5-nitrobenzamide; mp. 233.5° C.

EXAMPLE LXXXVI

To a stirred mixture of 4 parts of 3-(1,1-dimethylethyl)-2-hydroxy-6-methyl-5-nitrobenzoic acid, 8.3 parts of 4-amino-α-(2,4-dichlorophenyl)-2-(trifluoromethyl)benzeneacetonitrile and 66 parts of chlorobenzene are added 1.5 parts of phosphoryl chloride at 60° C. Stirring is continued for 2 hours at reflux temperature. The reaction mixture is cooled and poured onto trichloromethane. The whole is washed with water, dried, filtered and evaporated. The residue is dissolved in 150 parts of trichloromethane and petroleumether is added till turbid. The product is allowed to crystallize on standing. It is filtered off and recrystallized from a mixture of trichloromethane and petroleumether, yielding 4 parts of N-{4-[α-cyano-α-(2,4-dichlorophenyl)methyl]-3-(trifluoromethyl)phenyl}-3-(1,1-dimethylethyl)-2-hydroxy-6-methyl-5-nitrobenzamide; mp. 213.4° C.

EXAMPLE LXXXVII

To a stirred and hot (60° C) mixture of 4 parts of 3-(1,1-dimethlethyl)-2-hydroxy-6-methyl-5-nitrobenzoic acid, 6 parts of 4-amino-2-chloro-α-(4-chlorphenyl)-5-(1,1-dimethylethyl) benzeneacetronitrile and 66 parts of chlorobenzene is added 1 part of phosphoryl chloride, The whole is stirred and refluxed for 1 hour. After cooling, 300 parts of trichloromethane are added. The mixture is washed with a 5% sodium hydrogen carbonate solution and with water, dried, filtered and evaporated. The residue is purified by column-chromatography over silica gel using a mixture of trichloromethane, hexane and methanol (50:50:5) as eluent. The pure fractions are collected and the eluent is evaporated. The residue is crystallized from a mixture of trichloromethane and petroleumether. The product is filtered off and recrystallized from acetonitrile, yielding 2.3 parts of N-{5-chloro-4-[α-(4-chlorophenyl)-α-cyanomethyl]-2-(1,1-dimethylethyl)phenyl}-3-(1,1-dimethyl-ethyl)-2-hydroxy-6-methyl-5-nitrobenzamide; mp. 206.2° C.

EXAMPLE LXXXXVIII

To a stirred and hot (60° C) mixture of 4 parts of 3-(1,1-dimethylethyl)-2-hydroxy-56-methyl-5-nitrobenzoic acid, 7.7 parts of 4-amino-2-chloro-α-(4-chlorophenyl)-5-(1-methylethyl)-benzeneacetonitrile and 66 parts of chlorobenzene are added 1.5 parts of phosphoryl chloride. The whole is stirred and refluxed for 2 hours. The reaction mixture is cooled and poured onto 300 parts of trichloromethane. The whole is saturated with gaseous hydrogen chloride and filtered over hyflo. The filtrate is washed with a sodium hydrogen carbonate solution and with water, dried, filtered and evaporated. The residue is crystallized from a mixture of trichloromethane and petroleumether. The product is is filtered off and dried, yielding 6.3 parts (72%) of N-{5-chloro-4-[α-(4-chlorophenyl)α-cyanomethyl]-2-(1-methylethyl)phenyl}-3-(1,1-dimethyl)-2-hydroxy-6-methyl-5-nitrobenzamide; mp. 205.3° C.

EXAMPLE LXXXIX

This example illustrates the fasciolicidal activity of the compounds of formula (I). The compounds described below are highly potent agents against Fasciola hepatica in sheep as is apparent from the results obtained in the following test procedure.

Adult sheep with body weight between 21 and 51 kg were infected with 300 metacercaria and 13 weeks thereafter the same animals were treated with a single oral dose of 5 mg/kg of the compound under investigation. Eight days after treatment the animals were slaughtered, the liver and the gall-bladder removed, and the number of adult flukes present in both organs were counted. In a series of 22 control animals, receiving only solvent, the mean number of adult flukes found in both the liver and the gall-bladder was 116.

The following table gives the structures of a number of the claimed compounds and their efficacy at a single oral dose of 5 mg/kg. Efficacy is expressed in percent reduction of flukes found as compared to the controls ($n$ =22, number of flukes =116).

All compounds were dissolved in polyethylene glycol 200, the control animals therefore received the polyethylene glycol alone.

The compounds listed in the following table are not given for the purpose of limiting the invention thereto, but only to exemplify the useful fasciolicidal properties of all the compounds within the scope of formula (I).

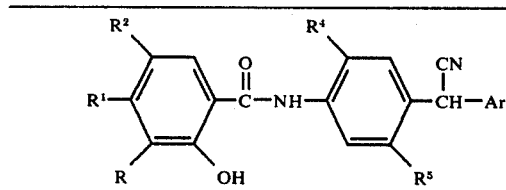

| R¹ | R² | R | R⁴ | R⁵ | Ar | % efficacy |
|---|---|---|---|---|---|---|
| H | I | I | H | H | C₆H₅ | 100 |
| H | I | I | H | H | 4-F—C₆H₄ | 100 |
| H | I | I | H | H | 4-Cl—C₆H₄ | 98 |
| H | I | I | H | H | 2,4-Cl₂—C₆H₃ | 70 |
| H | I | I | H | H | 3-CH₃—C₆H₄ | 89 |
| H | I | I | H | H | 4-CH₃—C₆H₄ | 85 |
| H | I | I | H | CN | 4-Cl—C₆H₄ | 44 |
| H | I | I | H | Cl | C₆H₅ | 70 |
| H | I | I | H | Cl | 3-Cl—C₆H₄ | 100 |
| H | I | I | H | Cl | 4-Cl—C₆H₄ | 98 |
| H | I | I | H | Cl | 2,4-Cl₂—C₆H₃ | 95 |
| H | I | I | H | Cl | 3,4-Cl₂—C₆H₃ | 99 |
| H | I | I | H | Cl | 3-CF₃—C₆H₄ | 96 |
| H | I | I | H | Cl | 3-CF₃—4-Cl—C₆H₃ | 100 |
| H | I | I | H | CF₃ | C₆H₅ | 90 |
| H | I | I | H | CF₃ | 4-F—C₆H₄ | 100 |
| H | I | I | H | CF₃ | 4-Cl—C₆H₄ | 100 |
| H | I | I | H | CF₃ | 4-Br—C₆H₄ | 100 |
| H | I | I | H | CF₃ | 2,4-Cl₂—C₆H₃ | 94 |
| H | I | I | H | CF₃ | 2,6-Cl₂—C₆H₃ | 86 |
| H | I | I | H | CF₃ | 4-CH₃—C₆H₄ | 70 |
| H | I | I | H | CF₃ | 4-OCH₃—C₆H₄ | 75 |
| H | I | I | H | CF₃ | 3-CF₃—C₆H₄ | 100 |
| H | I | I | H | CF₃ | 3-CF₃—4-Cl—C₆H₃ | 100 |
| H | I | I | CH₃ | Cl | 4-Cl—C₆H₄ | 100 |

-continued

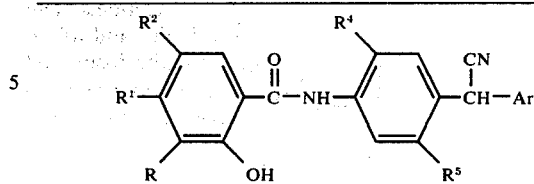

| R¹ | R² | R | R⁴ | R⁵ | Ar | % efficacy |
|---|---|---|---|---|---|---|
| Cl | Cl | Cl | H | H | C₆H₅ | 89 |
| Cl | Cl | Cl | H | H | 4-F—C₆H₄ | 81 |
| Cl | Cl | Cl | H | H | 4-Cl—C₆H₄ | 47 |
| Cl | Cl | Cl | H | H | 2,4-Cl₂—C₆H₃ | 100 |
| Cl | Cl | Cl | H | H | 3-CH₃—C₆H₄ | 81 |
| Cl | Cl | Cl | H | H | 4-CH₃—C₆H₄ | 84 |
| Cl | Cl | Cl | H | Cl | C₆H₅ | 60 |
| Cl | Cl | Cl | H | Cl | 3-Cl—C₆H₄ | 100 |
| Cl | Cl | Cl | H | Cl | 4-Cl—C₆H₄ | 100 |
| Cl | Cl | Cl | H | Cl | 2,4-Cl₂—C₆H₃ | 94 |
| Cl | Cl | Cl | H | Cl | 3,4-Cl₂—C₆H₃ | 93 |
| Cl | Cl | Cl | H | Cl | 3-CF₃—C₆H₄ | 100 |
| Cl | Cl | Cl | H | Cl | 3-CF₃—4-Cl—C₆H₃ | 100 |
| Cl | Cl | Cl | H | CF₃ | C₆H₅ | 88 |
| Cl | Cl | Cl | H | CF₃ | 4-F—C₆H₄ | 93 |
| Cl | Cl | Cl | H | CF₃ | 4-Cl—C₆H₄ | 98 |
| Cl | Cl | Cl | H | CF₃ | 4-Br—C₆H₄ | 100 |
| Cl | Cl | Cl | H | CF₃ | 2,4-Cl₂—C₆H₃ | 86 |
| Cl | Cl | Cl | H | CF₃ | 4-CH₃—C₆H₄ | 95 |
| Cl | Cl | Cl | H | CF₃ | 4-OCH₃—C₆H₄ | 94 |
| Cl | Cl | Cl | H | CF₃ | 3-CF₃—C₆H₄ | 98 |
| Cl | Cl | Cl | H | CF₃ | 3-CF₃—4-Cl—C₆H₃ | 89 |
| Cl | Cl | Cl | CH₃ | Cl | 4-Cl—C₆H₄ | 93 |
| Cl | Cl | Cl | CH₃ | Cl | 2,4-Cl₂—C₆H₃ | 86 |

EXAMPLE XC

This example is intended to demonstrate the useful activity of the compounds of formula (I) against Oestrus ovis and Haemonchus contortus in sheep. The experimental procedure was as follows:

24 Sheep were selected on clinical signs of Oestrus ovis infestation. Before commencement of the trial, 15 sheep of this group were treated orally with mebendazole at a dose of 15 mg/kg, in preparation for artificial infestations with Haemonchus contortus. 9 Sheep were not treated as above. The group of 15 sheep were then artificially infested with a daily dose of about 300 L₄ Haemonchus contortus larvae for 9 consecutive days (day −11 to day −3). On day 0 all 24 sheep were weighed and randomly allocated to 3 groups. Group I was left untreated as controls. Group II and III were treated respectively with:

compound A: N-{5-chloro-4-[α-(4-chlorophenyl)-α-cyanomethyl]-2-methylphenyl}-2-hydroxy-3,5-diiodobenzamide; and 3′-chloro-α-(p-chlorophenyl)-α-cyano-3,5-diiodo-p-salicylotoluidide.

The compounds tested were administered by intramuscular injection of a 5% injectable solution at a dose of 2.5 mg/kg live mass. The injectable solution used in the test had the following composition:

| Active ingredient | 5 | g |
|---|---|---|
| N-methylglucamine | 5 | g |
| Polyethylene glycol 400 | 15 | ml |
| Ethylenediamine tetraacetate disodium salt | 0.1 | g |
| Water ad. | 100.0 | ml |

The 8 control animals were slaughtered on day +10 and the 16 treated animals on +11. At the day of slaughter Haemonchus contortus worms were recovered from the abomasum and small intestines. The heads of all sheep were split longitudinally and all sinuses and turbinates were macroscopically inspected for all stages of Oestrus ovis. The number of Haemonchus contortus worms and Oestrus ovis larvae found in each sheet are tabulated in the following table:

| Treatment | Sheep number | Recovery of worms and larvae. Larvae of O. ovis recovered (instars) | | | $L_4H$. contortus recovered |
|---|---|---|---|---|---|
| | | 1st | 2nd + 3rd | total | |
| Controls | 447 | 0 | 3 | 3 | — |
| | 448 | 0 | 7 | 7 | — |
| | 449 | 0 | 19 | 19 | — |
| | 733 | 0 | 3 | 3 | 290 |
| | 428 | 0 | 0 | 0 | 400 |
| | 432 | 1 | 1 | 2 | 197 |
| | 429 | 7 | 4 | 11 | 410 |
| | 427 | 0 | 0 | 0 | 230 |
| Compound A 2.5 mpk i.m. | 445 | 0 | 0 | 0 | — |
| | 444 | 0 | 0 | 0 | — |
| | 442 | 0 | 0 | 0 | — |
| | 405 | 0 | 0 | 0 | 0 |
| | 435 | 0 | 0 | 0 | 2 |
| | 430 | 0 | 0 | 0 | 4 |
| | 436 | 0 | 0 | 0 | 0 |
| | 437 | 0 | 0 | 0 | 7 |
| Compound B | 446 | 0 | 0 | 0 | — |
| | 443 | 0 | 0 | 0 | — |
| | 450 | 0 | 0 | 0 | — |
| | 412 | 0 | 0 | 0 | 3 |
| 2.5 mpk i.m. | 718 | 0 | 0 | 0 | 3 |
| | 410 | 0 | 0 | 0 | 3 |
| | 420 | 0 | 0 | 0 | 2 |
| | 431 | 0 | 0 | 0 | 2 |

EXAMPLE XCI

The fasciolicidal activity of a number of the compounds of formula (I) in sheep was investigated following the same test procedure as described in Example LXXXIX except that the drugs were injected intramuscularly at a dose of 2.5 mg/kg live mass. Injectable solutions of the tested compounds had the same composition as described in Example XC.

The following table gives the structures of a number of the claimed compounds and their efficacy at a single intramuscular dose of 2.5 mg/kg live mass. Efficacy is expressed in percent reduction of flukes found as compared to the controls.

It is to be understood that the compounds listed in the following table are not given for the purpose of limiting the invention thereto but in order to exemplify the useful flukicidal properties of all the compounds within the scope of formula I.

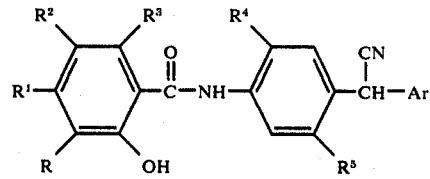

| R | $R^1$ | $R^2$ | $R^3$ | $R^4$ | $R^5$ | Ar | %efficacy |
|---|---|---|---|---|---|---|---|
| Cl | — | $NO_2$ | OH | — | $CF_3$ | 2,4-$(Cl)_2$—$C_6H_3$ | 42 |
| — | — | — | OH | — | $CF_3$ | 4-Cl—$C_6H_4$ | 72 |
| — | — | — | OH | — | $CF_3$ | 4-$(CH_3)$—$C_6H_4$ | 71 |
| — | — | — | OH | — | $CF_3$ | 4-$(OCH_3)$—$C_6H_4$ | 83 |
| — | — | — | OH | — | $CF_3$ | 4-F—$C_6H_4$ | 75 |
| — | — | — | OH | — | $CF_3$ | 2,4-$(Cl)_2$—$C_6H_3$ | 71 |
| — | — | $NO_2$ | OH | — | $CF_3$ | 2,4-$(Cl)_2$—$C_6H_3$ | 45 |
| — | — | — | OH | — | CN | 4-Cl—$C_6H_4$ | 79 |
| — | — | — | OH | — | $CF_3$ | 4-Br—$C_6H_4$ | 57 |
| — | — | — | OH | — | — | 4-F—$C_6H_4$ | 96 |
| — | — | — | OH | — | — | 4-$(CH_3)$—$C_6H_4$ | 85 |
| — | — | — | — | — | — | $C_6H_5$ | 60 |
| — | — | — | OH | — | Cl | $C_6H_5$ | 75 |
| — | — | — | OH | — | — | $C_6H_5$ | 73 |
| — | — | — | OH | — | — | 4-$(OCH_3)$—$C_6H_4$ | 71 |
| — | — | — | OH | — | Cl | 3-$(CF_3)$—$C_6H_4$ | 100 |
| — | — | — | — | — | — | 4-$(CH_3)$—$C_6H_4$ | 69 |
| I | — | I | — | — | Cl | 2-naphthalenyl | 99 |
| Cl | Cl | Cl | — | — | Cl | 2-naphthalenyl | 99 |
| Cl | Cl | Cl | — | — | $CF_3$ | 2-naphthalenyl | 84 |
| Cl | Cl | Cl | — | $CH_3$ | Cl | 5-Cl—2-thienyl | 61 |
| I | — | I | — | $CH_3$ | Cl | 5-Cl—2-thienyl | 92 |
| Cl | Cl | Cl | — | — | Cl | 5-Cl—2-thienyl | 62 |
| I | — | I | — | — | Cl | 5-Cl—2-thienyl | 87 |
| t.$C_4H_9$ | — | $NO_2$ | $CH_3$ | — | Cl | 4-Cl—$C_6H_4$ | 91 |
| t.$C_4H_9$ | — | $NO_2$ | $CH_3$ | $CH_3$ | Cl | 4-Cl—$C_6H_4$ | 100 |
| t.$C_4H_9$ | — | $NO_2$ | $CH_3$ | Cl | Cl | 4-Cl—$C_6H_4$ | 100 |
| t.$C_4H_9$ | — | $NO_2$ | $CH_3$ | — | $CF_3$ | 3-$(CF_3)$—$C_6H_4$ | 98 |
| t.$C_4H_9$ | — | $NO_2$ | $CH_3$ | — | $CF_3$ | 4-Cl—$C_6H_4$ | 85 |
| t.$C_4H_9$ | — | $NO_2$ | $CH_3$ | — | $CF_3$ | 4-Br—$C_6H_4$ | 92 |
| t.$C_4H_9$ | — | $NO_2$ | $CH_3$ | $CH_3$ | Cl | 2,4-$(Cl)_2$—$C_6H_3$ | 68 |
| t.$C_4H_9$ | — | $NO_2$ | $CH_3$ | — | $CF_3$ | 2,4-$(Cl)_2$—$C_6H_3$ | 67 |
| I | — | I | — | t.$C_4H_9$ | Cl | 4-Cl—$C_6H_4$ | 100 |
| t.$C_4H_9$ | — | $NO_2$ | $CH_3$ | — | Cl | 3-$(CF_3)$—$C_6H_4$ | 70 |
| Cl | Cl | Cl | — | t.$C_4H_9$ | Cl | 4-Cl—$C_6H_4$ | 100 |
| t.$C_4H_9$ | — | $NO_2$ | $CH_3$ | t.$C_4H_9$ | Cl | 4-Cl—$C_6H_4$ | 100 |
| t.$C_4H_9$ | — | $NO_2$ | $CH_3$ | — | — | 2,4-$(Cl)_2$—$C_6H_3$ | 61 |
| Cl | Cl | Cl | — | i.$C_3H_7$ | Cl | 4-Cl—$C_6H_4$ | 63 |
| I | — | I | — | i.$C_3H_7$ | Cl | 4-Cl—$C_6H_4$ | 100 |

-continued

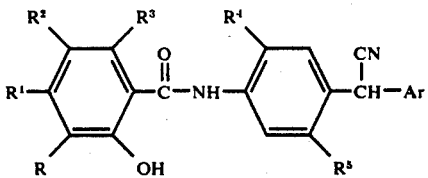

| R | R¹ | R² | R³ | R⁴ | R⁵ | Ar | %efficacy |
|---|----|----|----|----|----|----|-----------|
| t.C₄H₉ | — | NO₂ | CH₃ | i.C₃H₇ | Cl | 4-Cl—C₆H₄ | 51 |

EXAMPLE XCII

This example illustrates the effectiveness of the compounds of this invention against Hypoderma bovis in cattle.

The test is carried out with naturally infected cattle showing visible warbles caused by Hypoderma bovis. The animals are shaved on their back to make the marbles clearly visible for counting. Treatment is given by intramuscular injection of a 5% injectable solution of N-{5-chloro-4-[α-(4-chlorophenyl)-α-cyanomethyl]-2-methylphenyl}-2-hydroxy-3,5-diiodobenzamide having the composition described in Example XC.

Ten days after treatment, the grubs are pressed out of the warbles and examined for being alive or dead. This examination is done by direct observation of the larvae's further evolution, in an artificial environment, to the pupa stage and finally to the imago.

The results obtained in this experiment are given in the following table.

Activity of
N-{5-chloro-4-[α-(4-chlorophenyl)-α-cyanomethyl]-2-methylphenyl}-2-hydroxy-3,5-diiodobenzamide by intramuscular injection on Hypoderma bovis in cattle

| Cattle No. | Weight in kg | Dose mpk | Activity control 10 days after treatment Grubs died/Grubs extracted |
|-----------|--------------|----------|-----|
|   | 285 | 2.5 | 12/15 |
| 2 | 191 | 2.5 | 5/6 |
| 3 | 220 | 2.5 | 1/3 |
| 4 | 291 | 2.5 | 4/7 |
| 5 | 244 | 5 | 5/5 |
| 6 | 190 | 5 | 5/5 |
| 7 | 456 | 5 | 5/5 |
| 8 | 364 | 5 | 3/3 |

EXAMPLE XCIII

A mixture of 8.75 parts of 4-amino-2-α-(4-chlorophenyl)-5-methylbenzeneacetonitrile, 2.10 parts of phosphorous trichloride and 176 parts of chlorobenzene is stirred and refluxed for 2 hours. After cooling to 60° C, there are added 11.7 parts of 2-hydroxy-3,5-diiodobenzoic acid and the whole is heated to 115° C. Stirring is continued for 2 hours at 115° C. The reaction mixture is filtered while hot. The product is allowed to crystallize from the filtrate at room temperature. It is filtered off and dried, yielding 10.5 parts (52.8%) of N-{5-chloro-4-[α-(4-chlorophenyl)-α-cyanomethyl]-2-methylphenyl}-2-hydroxy-3,5-diodobenzamide; mp. 217° C.

EXAMPLE XCIV

To a stirred mixture of 4.14 parts of 2-hydroxybenzoic acid, 8.75 parts of 4-amino-2-chloro-α-(4-chloropenyl)-5-methylbenzeneacetonitrile and 176 parts of chlorobenzene are added 2.8 parts of phosphorous trichloride. The whole is stirred and refluxed for 1.50 hours. The reaction mixture is cooled to room temperature and 132 parts of hexane are added while stirring vigorously. Upon standing overnight at room temperature, the product is crystallized. It is filtered off and dried in vacuo at 50° C, yielding 10 parts (81.3%) of N-{5-chloro-4-[α-(4-chlorophenyl)-α-cyanomethyl]-2-methylphenyl}-2-hydroxybenzamide; mp. 183–186.5° C.

To a stirred mixture of 8.22 parts of N-{5-chloro-4-[α-(4-chlorophenyl)-α-cyanomethyl]-2-methylphenyl}-2-hydroxybenzamide and 40 parts of acetic acid are added quickly 12.9 parts of an iodine monochloride solution in acetic acid. After the addition of 86 parts of water, the whole is stirred for 45 minutes at 80° C. The reaction mixture is cooled to about 17° C. The precipitated product is filtered off, washed successively with 20 parts of water, 20 parts of acetic acid and again with 20 parts of water, and stirred for 30 minutes with 80 parts of 2-propanone. Then there are added 150 parts of water and stirring is continued for 1 hour. The product is filtered off, washed with water and crystallized from chlorobenzene, yielding 7.5 parts (76.3%) of N-{5-chloro-4-[α-(4-chlorophenyl)-α-cyanomethyl]-2-methylphenyl}-2-hydroxy-3,5-diodobenzamide; mp. 214°–216° C.

We claim:
1. A chemical compound selected from the group consisting of a salicylanilide having the formula:

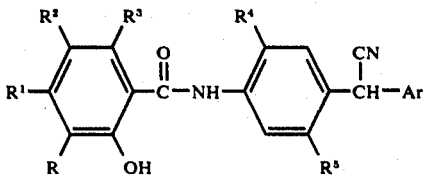

and the pharmaceutically acceptable salts thereof, wherein:
R is a member selected from the group consisting of hydrogen, halo, lower alkyl and nitro;
R¹ is a member selected from the group consisting of hydrogen and halo;
R² is a member selected from the group consisting of hydrogen, halo, lower-alkyl and nitro;
R³ is a member selected from the group consisting of hydrogen, hydroxy and lower alkyl, provided that when said $R^3$ is hydroxy or lower alkyl then said $R^1$ is hydrogen;

$R^4$ is a member selected from the group consisting of hydrogen, halo and lower alkyl;

$R^5$ is a member selected from the group consisting of hydrogen, halo, lower alkyl, cyano and trifluoromethyl; and Ar is a member selected from the group consisting of phenyl, substituted phenyl, thienyl, halothienyl and naphthalenyl, wherein said "substituted phenyl" represents phenyl having from 1 to 3 substituents independently selected from the group consisting of halo, lower alkyl, lower alkyloxy and trifluoromethyl.

2. A chemical compound selected from the group consisting of N-{5-chloro-4-[α-(4-chlorophenyl)-α-cyanomethyl]-2-methylphenyl}-2-hydroxy-3,5-diiodobenzamide and the pharmaceutically acceptable salts thereof.

3. A chemical compound selected from the group consisting of 3'-chloro-α-(p-chlorophenyl)-α-cyano-3,5-diiodo-p-salicylotoluidide and the pharmaceutically acceptable salts thereof.

4. N-{5-chloro-4-[α-(4-chlorophenyl)-α-cyanomethyl]-2-methylphenyl}-2-hydroxy-3,5-diiodobenzamide.

5. 3'-chloro-α-(p-chlorophenyl)-α-cyano-3,5-diiodo-p-salicylotoluidide.

6. An antiparasitic composition comprising an effective antiparasitic amount of a compound selected from the group consisting of a salicylanilide having the formula:

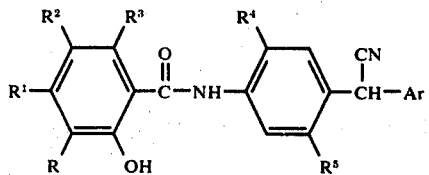

and the pharmaceutically acceptable salts thereof, wherein:

R is a member selected from the group consisting of hydrogen, halo, lower alkyl and nitro;

$R^1$ is a member selected from the group consisting of hydrogen and halo;

$R^2$ is a member selected from the group consisting of hydrogen, halo, lower alkyl and nitro;

$R^3$ is a member selected from the group consisting of hydrogen, hydroxy and lower alkyl, provided that when said $R^3$ is hydroxy or lower alkyl then said $R^1$ is hydrogen;

$R^4$ is a member selected from the group consisting of hydrogen, halo and lower alkyl;

$R^5$ is a member selected from the group consisting of hydrogen, halo, lower alkyl, cyano and trifluoromethyl; and Ar is a member selected from the group consisting of phenyl, substituted phenyl, thienyl, halothienyl and naphthalenyl, wherein said "substituted phenyl" represents phenyl having from 1 to 3 substituents independently selected from the group consisting of halo, lower alkyl, lower alkyloxy and trifluoromethyl, in admixture with a pharmaceutically acceptable carrier.

7. The composition of claim 6 wherein the compound is a member selected from the group consisting of N-{5-chloro-4-[α-(4-chlorophenyl)-α-cyanomethyl]-2-methylphenyl}-2-hydroxy3,5-diiodobenzamide and the pharmaceutically acceptable salts thereof.

8. The composition of claim 6 wherein the compound is a member selected from the group consisting of 3'-chloro-α-(p-chlorophenyl)-α-cyano-3,5-diiodo-p-salicylotoluidide and the pharmaceutically acceptable salts thereof.

9. A method of killing parasites which comprises treating infected subjects with an antiparasitically effective amount of a compound selected from the group consisting of a salicylanilide having the formula:

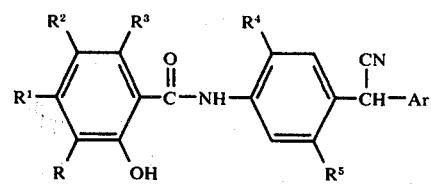

and the pharmaceutically acceptable salts thereof, wherein:

R is a member selected from the group consisting of hydrogen, halo, lower alkyl and nitro;

$R^1$ is a member selected from the group consisting of hydrogen and halo;

$R^2$ is a member selected from the group consisting of hydrogen, halo, lower alkyl and nitro;

$R^3$ is a member selected from the group consisting of hydrogen, hydroxy and lower alkyl, provided that when said $R^3$ is hydroxy or lower alkyl then said $R^1$ is hydrogen;

$R^4$ is a member selected from the group consisting of hydrogen, halo and loweralkyl;

$R^5$ is a member selected from the group consisting of hydrogen, halo, lower alkyl, cyano and trifluoromethyl; and Ar is a member selected from the group consisting of phenyl, substituted phenyl, thienyl, halothienyl and naphthalenyl, wherein said substituted phenyl represents phenyl having from 1 to 3 substituents independently selected from the group consisting of halo, lower alkyl, lower alkyloxy and trifluoromethyl.

10. The method of claim 9 wherein the compound is a member selected from the group consisting of N-{5-chloro-4-[α-(4-chlorophenyl)-α-cyanomethyl]-2-methylphenyl}-2-hydroxy-3,5-diiodobenzamide and the pharmaceutically acceptable salts thereof.

11. The method of claim 9 wherein the compound is a member selected from the group consisting of 3'-chloro-α-(p-chlorophenyl)-α-cyano-3,5-diiodo-p-salicylotoluidide and the pharmaceutically acceptable salts thereof.

* * * * *

UNITED STATES PATENT AND TRADEMARK OFFICE
CERTIFICATE OF CORRECTION

PATENT NO. : 4,005,218
DATED : Jan. 25, 1977
INVENTOR(S) : Marcel A.C. Janssen & Victor K. Sipido It is certified that error appears in the above-identified patent and that said Letters Patent are hereby corrected as shown below:

Column 5, line 27, "(VII)" should read ---(VIII)---
Column 28, line 60, "EXAMPLE LXXXXVIII' should read
  --- EXAMPLE LXXXVIII ---.
Column 30, line 53, "3'-chloro-" should read
  "compound B: 3'-chloro-"
Column 31, line 7, "sheet" should read ---sheep---
Column 33, line 46, under Cattle No. heading: the numeral
  1 should appear in the column.
Column 28, Line 62, "hydroxy-56-methyl" should read
  ---hydroxy-6-methyl---

Column 1, line 19, "British Pat. No. 1,183,461" should read
  --British Pat. No. 1,183,641--.

Signed and Sealed this

Eleventh Day of July 1978

[SEAL]

Attest:

RUTH C. MASON
Attesting Officer

DONALD W. BANNER
Commissioner of Patents and Trademarks